(12) United States Patent
Gao et al.

(10) Patent No.: US 9,446,544 B2
(45) Date of Patent: Sep. 20, 2016

(54) METHOD AND SYSTEM FOR MULTIVARIATE REMOTE MONITORING OF POLYMER PROCESSING

(75) Inventors: Robert X. Gao, Manchester, CT (US); Zhaoyan Fan, Willimantic, CT (US); David O. Kazmer, North Andover, MA (US)

(73) Assignees: University of Connecticut, Farmington, CT (US); University of Massachusetts, Boston, MA (US)

( * ) Notice: Subject to any disclaimer, the term of this patent is extended or adjusted under 35 U.S.C. 154(b) by 1107 days.

(21) Appl. No.: 13/538,475

(22) Filed: Jun. 29, 2012

(65) Prior Publication Data

US 2013/0030723 A1    Jan. 31, 2013

Related U.S. Application Data

(60) Provisional application No. 61/503,922, filed on Jul. 1, 2011.

(51) Int. Cl.
*G01N 33/00* (2006.01)
*B29C 45/77* (2006.01)
*G01N 33/44* (2006.01)

(52) U.S. Cl.
CPC ............ *B29C 45/77* (2013.01); *G01N 33/442* (2013.01); *B29C 2945/7604* (2013.01); *B29C 2945/76006* (2013.01); *B29C 2945/76461* (2013.01); *B29C 2945/76538* (2013.01); *B29C 2945/76993* (2013.01)

(58) Field of Classification Search
None
See application file for complete search history.

(56) References Cited

U.S. PATENT DOCUMENTS 3,937,776 A * 2/1976 Hold .................. B29C 45/76
264/328.13

OTHER PUBLICATIONS

Praher, B. et al., Non-invasive Ultrasound Based Reflection Measurements at Polymer Plastication Units: Measurement of Melt Temperature, Melting Behaviour and Screw Wear, Apr. 6, 2014, VDW Verlag GmbH, Sensoren und Messystem 03, pp. 1-6, ISBN 978-3-8007-3622-5.*
Notification of Transmittal of International Search Report and Written Opinion for PCT/US2012/045031 dated Jan. 31, 2014; entitled "Method and System for Multivariate Remote Monitoring of Polymer Processing".

(Continued)

*Primary Examiner* — Mischita Henson
(74) *Attorney, Agent, or Firm* — Hamilton, Brook, Smith & Reynolds, P.C.

(57) ABSTRACT

In an injection molding process, it can be difficult to detect, in real time, process control variables such as pressure and temperature. Traditional temperature detectors and pressure sensors can be difficult to place in or near a mold cavity. An example embodiment of the present invention includes a self-powered multivariate sensor and uses acoustic transmission. The sensor may employ an infra-red thermal detector and pressure sensor and transmit coded representations of measurements acoustically via a body of the mold. From the temperature and pressure, melt velocity and melt viscosity of a compound in the mold can be determined with a high degree of accuracy by a processor internal to or external from the sensor. The example embodiment maintains structural integrity of the mold, provides a wireless self-powered sensor, and makes available sensing of properties of the viscous compound to enable injection molded parts production at a success rate exceeding 90%.

37 Claims, 34 Drawing Sheets

(56) References Cited

OTHER PUBLICATIONS

Gao, R, et al., "A New Method for Determining Melt Front Velocity through Temperature Measurement", *Proceeding of the ASME Dynamic Systems and Control Conference*, Paper No. 6059, Arlington, VA, Oct. 31-Nov. 2, 2011.

Kazmer, D., et al, "Feasibility Analysis of an In-mold Multivariate Sensor", *Journal of International Polymer Processing*, vol. 26, No. 1, pp. 63-72, Oct. 2010.

Zhang, L., et al, "Design of a Wireless Sensor for Injection Molding Cavity Pressure Measurement," *Proceeding of the 4th National Science Foundation Design & Manufacturing Conference*, San Juan, Puerto Rico, 2002.

Theurer, C.B., et al, "Energy Extraction for a Self-Energized Pressure Sensor," *IEEE Sensors Journal*, vol. 4, No. 1, pp. 28-35, Feb. 2004.

Gao, R., et al., "Self-Powered Sensing for Mechanical System Condition Monitoring," *SPIE Smart Structures/NDE Joint Conference and International Symposium on Sensors and Smart Structures Technologies for Civil, Mechanical, and Aerospace Systems and Materials*, paper #5391-33, San Diego, CA, Mar. 14, 2004.

Gao, R., et al, "Coded Acoustic Wave Modulation for Multi-Parameter Transmission", *Instrumentation and Measurement Technology Conference, IEEE International*, May 13-16, 2012.

Gao, R., et al, "Multivaraite Sensing and Wireless Data Communication for Process Monitorning in RF-Shielded Environment"; *CIRP Annals—Manufacturing Technology*, 61:523-526, 2012.

Asadizanjani, N., et al. "Viscosity Measurement in Injection Molding Using a Multivariate Sensor" *Proceedings of the ASME 2012 International Symposium on Flexible Automation* St. Louis, MO, pp. 231-237, Jun. 18-20, 2012.

http://kazmer.uml.edu/research/omin.html "Multi-Modal Sensors for Polymer Processing" retrieved from Internet May 3, 2010.

International Preliminary Report on Patentability and Written Opinion dated Feb. 27, 2014 for PCT/US2012/045031 entitled "Method and System for Multivariate Remote Monitoring of Polymer Processing".

Gao, R., et al., "Injection Molding Process Monitoring Using a Self-Energized Dual Parameter Sensor", CIRP Annals—Manufacturing Technology 57:389-393, 2008.

Brown, E.C., et al. "Melt Temperature Field Measurement in Single Screw Extrusion Using Thermocouple Meshes" AIP Review of Scientific Instrument, 75:11, Nov. 2004.

Theurer, C., et al. "Passive Charge Modulation for a Wireless Pressure Sensor" IEEE Sensors Journal, 6:1, Feb. 2006.

Theurer, C., et al., "Threshold Energy Switching and Its Application to Wireless Sensing in High Energy Manufacturing Processes" Proceedings of IMECE2002; ASME International Mechanical Engineering Congress & Exposition, IMECE2002-33219; Nov. 17-22, 2002.

\* cited by examiner

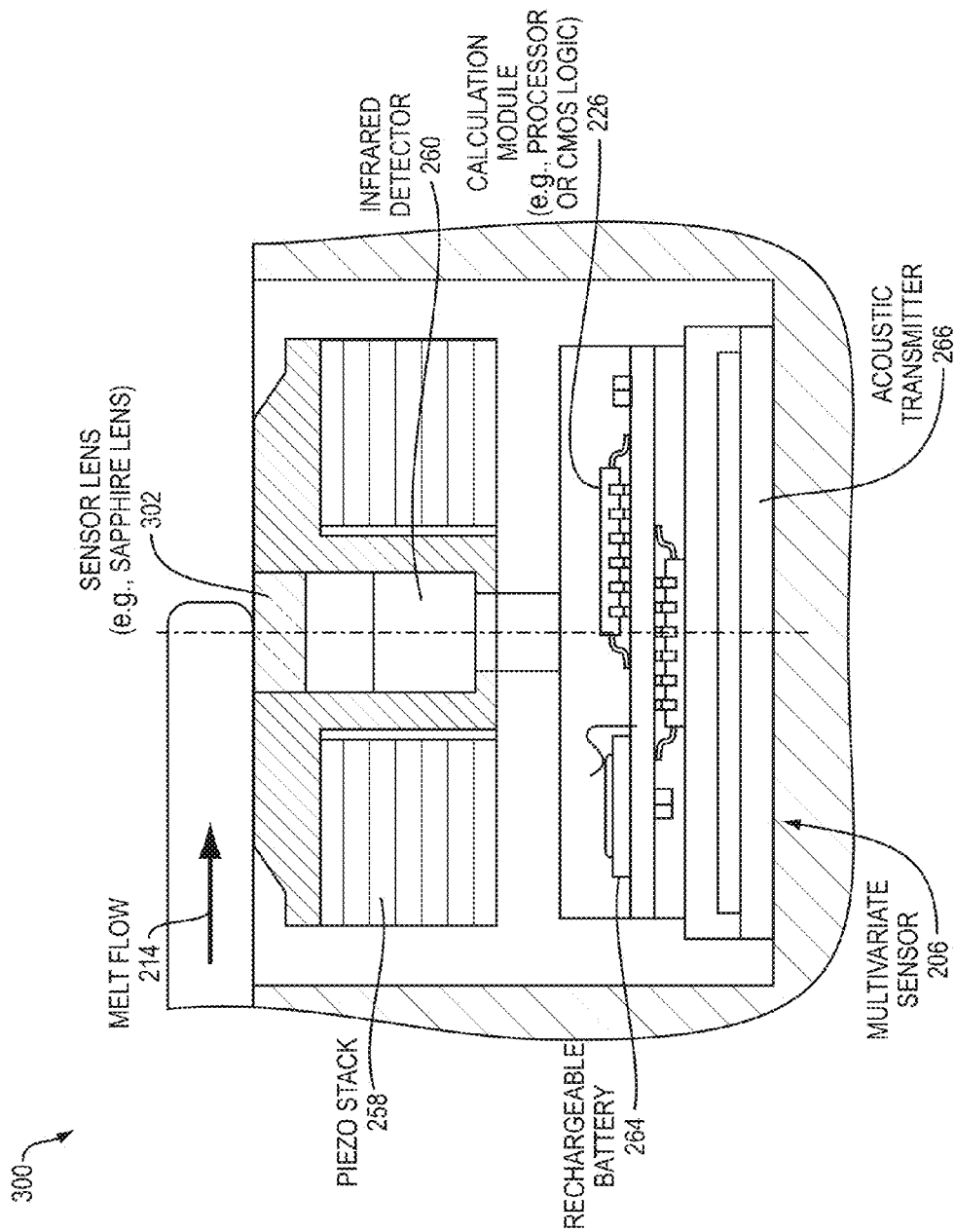

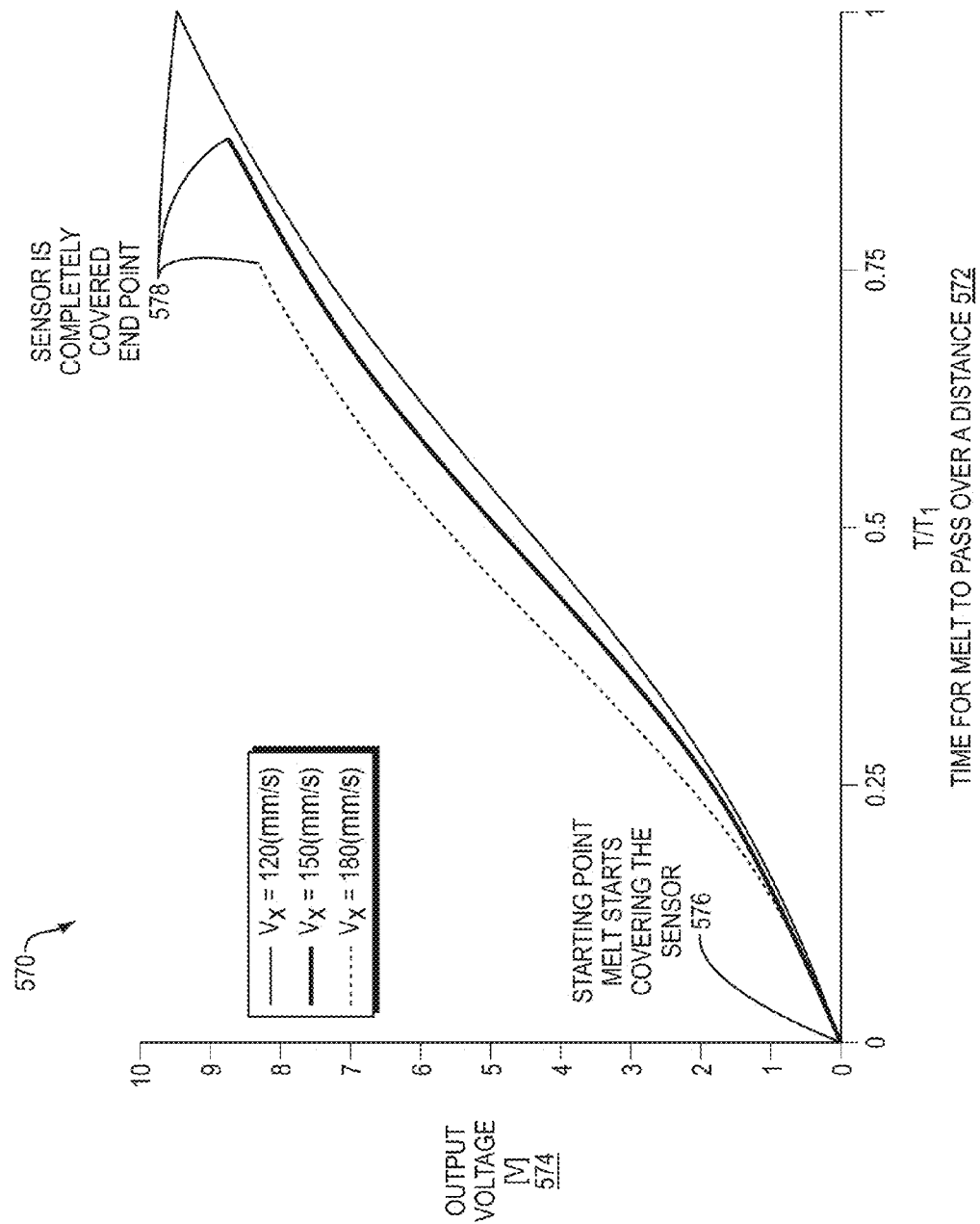

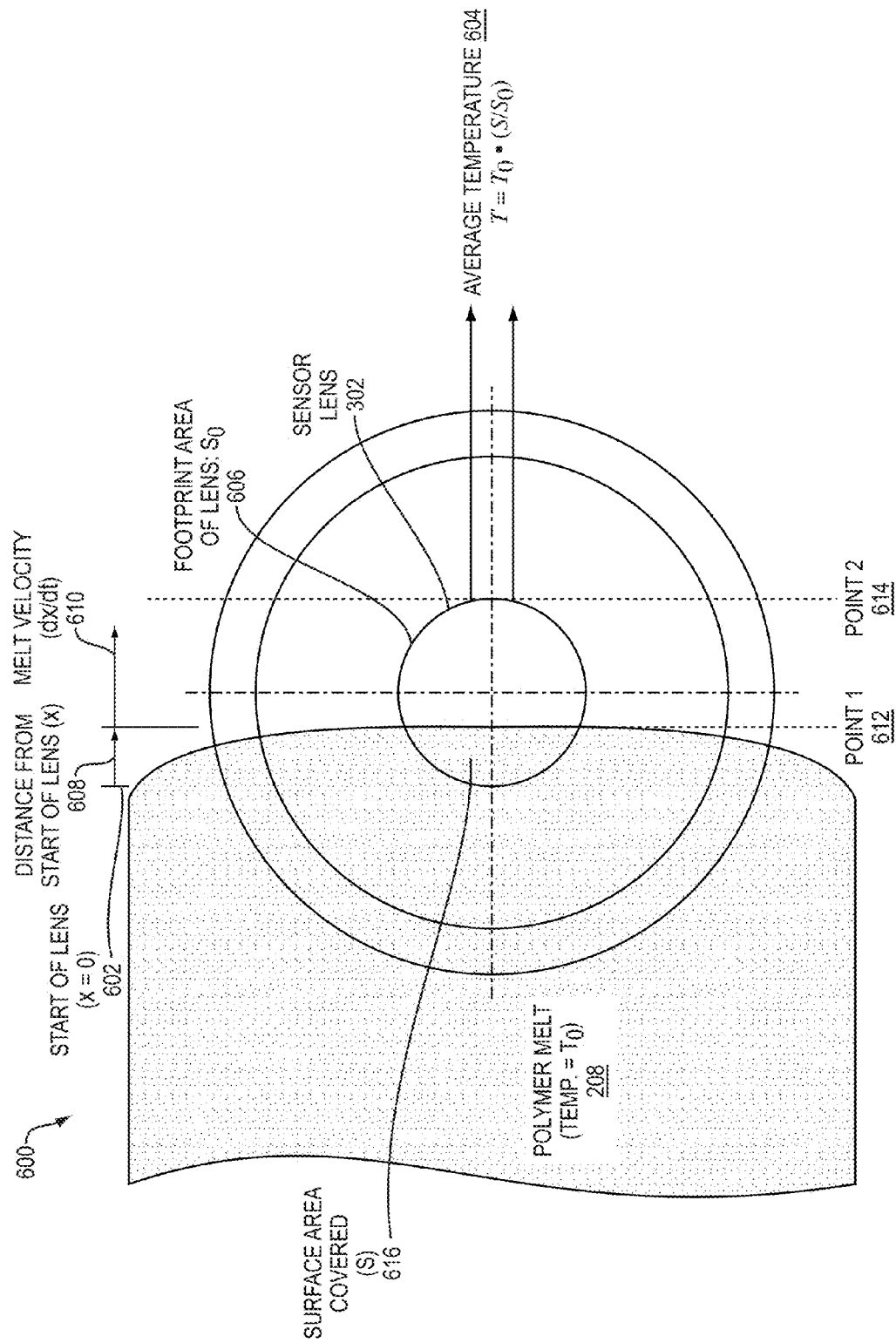

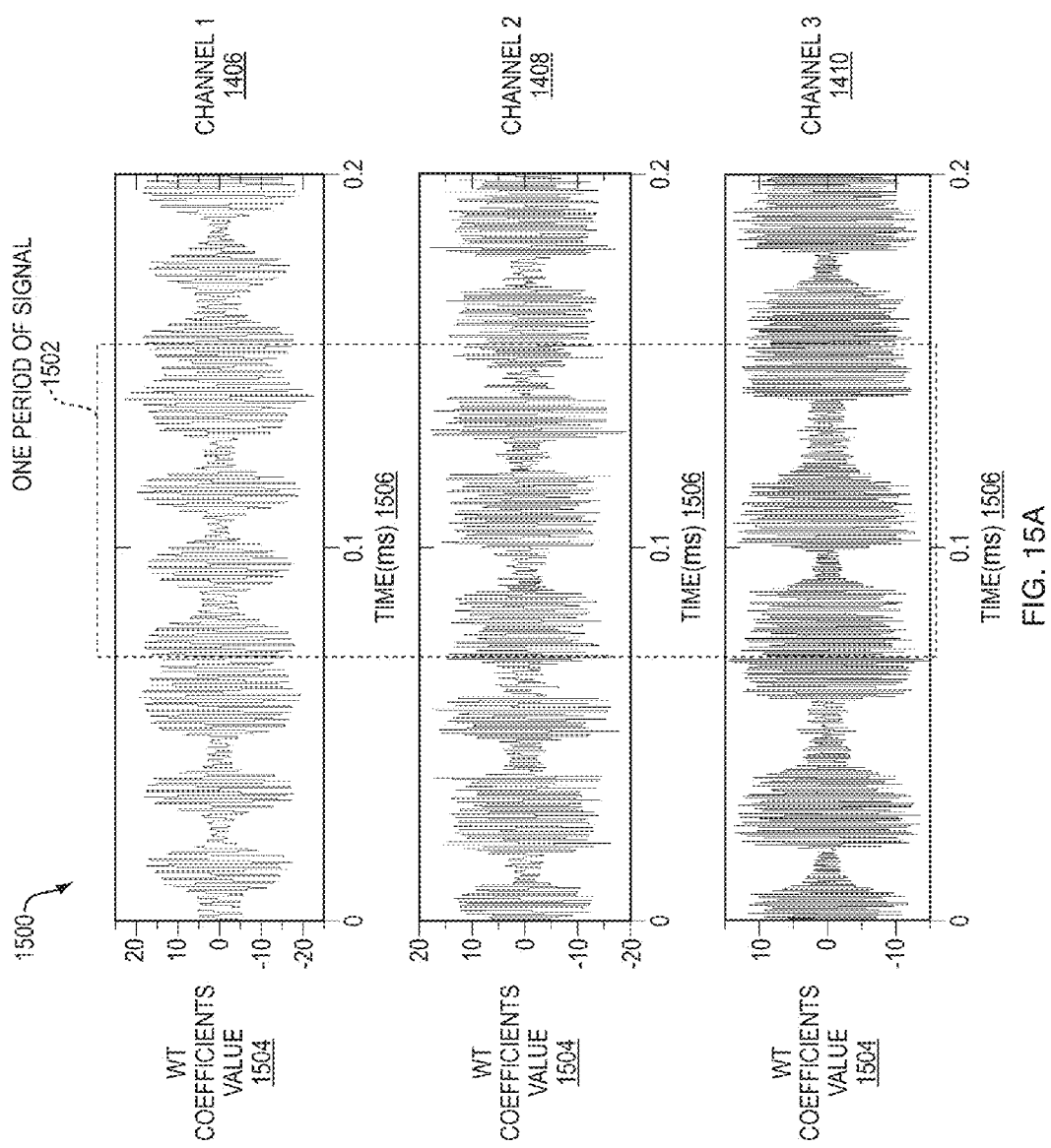

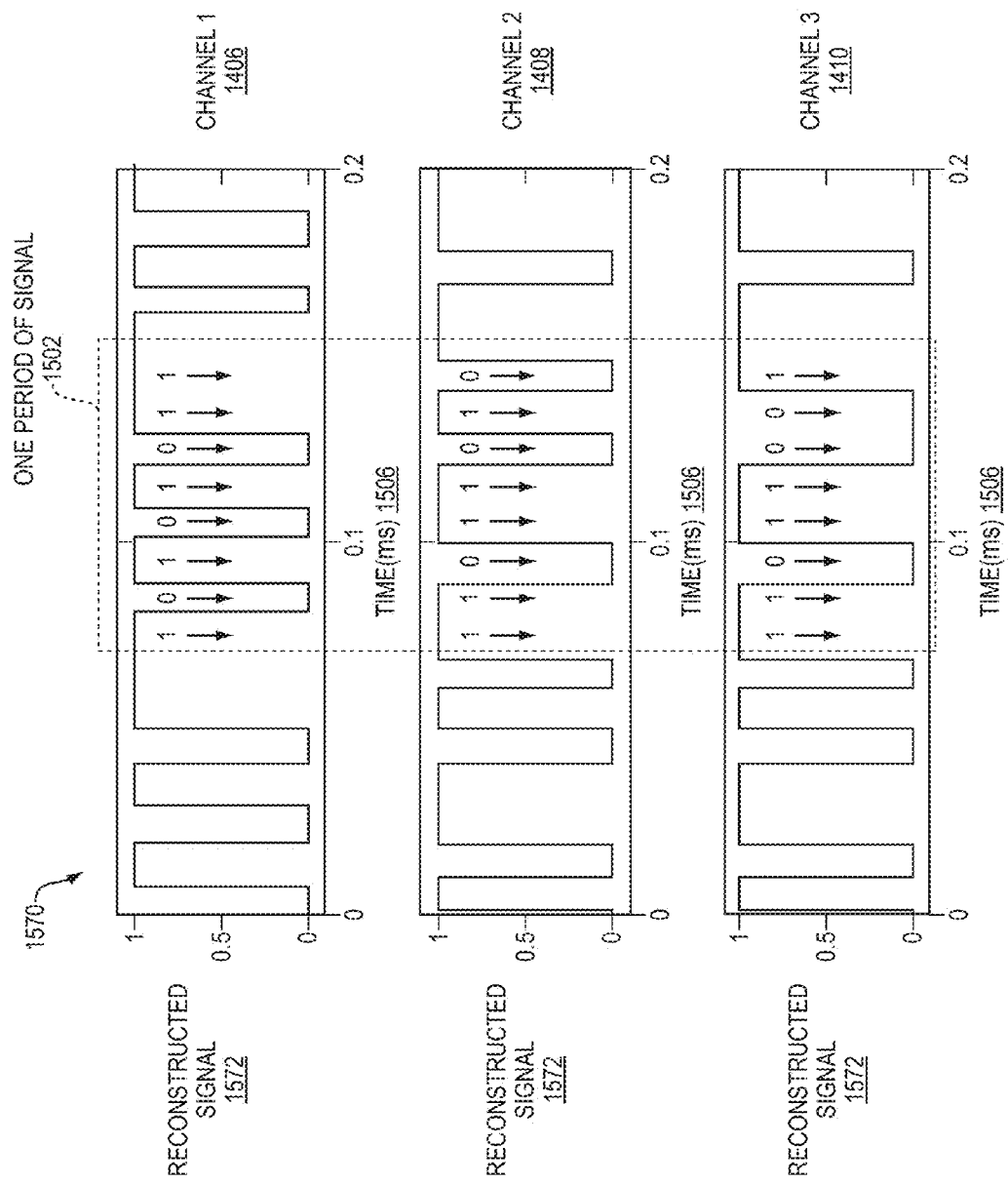

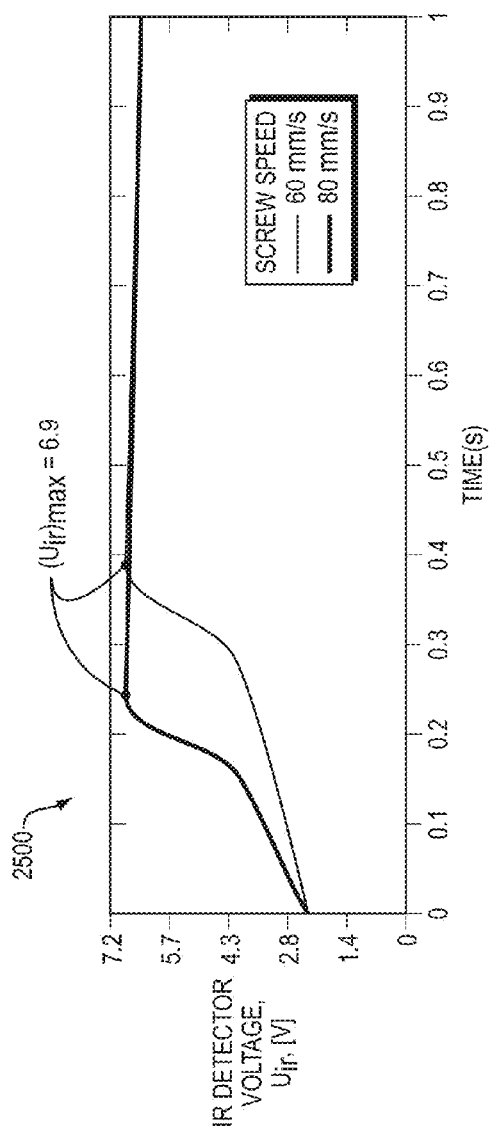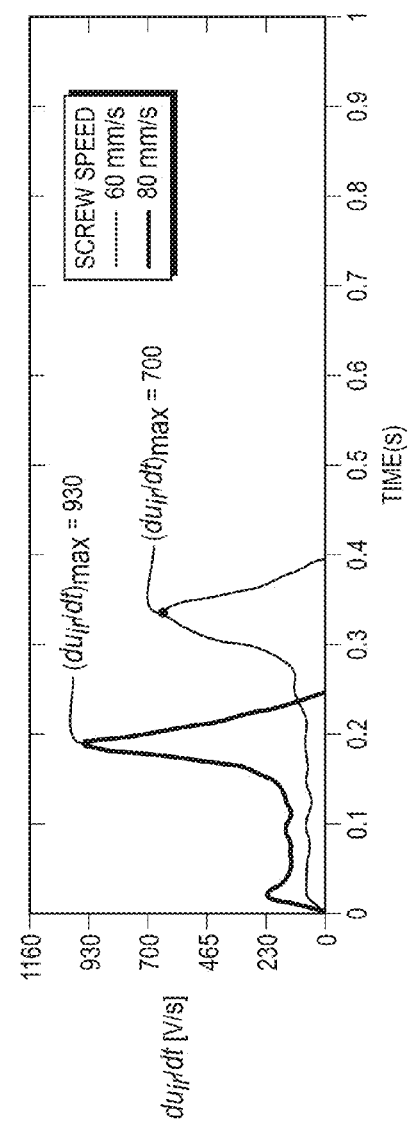
FIG. 25A
FIG. 25B

METHOD AND SYSTEM FOR MULTIVARIATE REMOTE MONITORING OF POLYMER PROCESSING

RELATED APPLICATION

This application claims the benefit of U.S. Provisional Application No. 61/503,922, filed on Jul. 1, 2011.

The entire teachings of the above application are incorporated herein by reference.

GOVERNMENT SUPPORT

This invention was made with government support under Grants # CMMI-1000816 and 1000507 from the National Science Foundation. The government has certain rights in the invention.

BACKGROUND OF THE INVENTION

Injection molding is a process of injecting a polymer mold into a mold cavity to form a manufactured object, such as a plastic part. As time in the injection molding process passes, properties inside the mold cavity dynamically change. These properties can include temperature, pressure, mold velocity, and mold viscosity.

SUMMARY OF THE INVENTION

In one embodiment of the present invention, a sensor may include an infra-red thermal detector. The sensor may further include a pressure sensor configured to produce charge as a function of pressure, where the charge is available as power to a circuit. The sensor may further include a processor configured to convert output from the thermal detector and pressure sensor and output coded representations of pressure, temperature, and melt velocity. The sensor may additionally include an acoustic transmitter configured to transmit the coded representations via an acoustic medium. The processor and acoustic transmitter may be powered by the charge produced by the pressure sensor.

In another embodiment, the processor may be configured to output a coded melt viscosity. The processor may output the coded representations by summing products of binary representations of pressure, temperature, and velocity and respective carrier waves.

In yet another embodiment, the sensor may further include an acoustic receiver configured to receive the coded representations via the acoustic medium and determine binary representations of pressure, temperature, and melt velocity. The acoustic receiver may be further configured to calculate melt viscosity as a function of melt velocity.

In some embodiments, the pressure sensor is a piezoelectric transducer.

In an example embodiment, an injection mold includes the sensor embedded within the injection mold. The thermal detector may be configured to monitor material in the injection mold.

In another example embodiment, a method of sensing includes detecting infra-red thermal data. The method further includes sensing pressure by producing a charge as a function of pressure. The charge may be available as power to a circuit. The method may further include converting output from the infra-red thermal data and from the sensed data. The method may additionally include outputting coded representations of pressure, temperature, and melt velocity. The method may further include transmitting the coded representations via an acoustic medium. The method may also include powering the converting, the outputting and the transmitting by the charge produced by the pressure sensor.

In another embodiment, a sensor includes an infra-red thermal detector. The sensor further includes a pressure sensor configured to produce charge as a function of pressure. The charge may be available as power to a circuit. The sensor further includes a processor configured to convert output from the thermal detector and pressure sensor and output coded representations of pressure and temperature. The sensor additionally includes an acoustic transmitter configured to transmit the coded representations in a carrier wave via an acoustic medium. The processor and acoustic transmitter may be powered by the charge produced by the pressure sensor.

In one embodiment, the processor may be further configured to output at least one of a coded melt velocity and a coded melt viscosity.

In another embodiment, the sensor includes an acoustic receiver configured to receive the coded representations via the acoustic medium and determine binary representations of pressure and temperature. The acoustic receiver may be further configured to calculate melt velocity as a function of temperature and melt viscosity as a function of melt velocity.

In one embodiment, a method includes detecting infra-red thermal data. The method further includes sensing pressure by producing a charge as a function of pressure. The charge may be available as power to a circuit. The method may further include converting output from the infra-red thermal data and from the sensed data. The method may further include outputting coded representations of pressure and temperature. The method may additionally include transmitting the coded representations in a carrier wave via an acoustic medium. The method further includes powering the converting, the outputting, and the transmitting by the charge produced by the pressure sensor.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3A is a block diagram illustrating an example embodiment of a multivariate sensor equipped with a piezo stack, the infrared detector, a calculation module, and an acoustic transmitter.

FIG. 5C is a diagram illustrating an example embodiment of output voltage of an infrared detector graphed over time for the melt to pass over a distance.

FIG. 6 is a diagram of a polymer melt moving over a sensor of an infrared detector.

FIG. 15A is a diagram illustrating different WT coefficients for center frequencies of each channel.

FIG. 15C is a diagram illustrating an example embodiment of thresholding to differentiate individual "0" and "1" bits to extract the digital data from filtered signals.

FIGS. 25A-B are block diagrams illustrating measured voltage from an infrared detector.

DETAILED DESCRIPTION OF THE INVENTION

Figure 1:
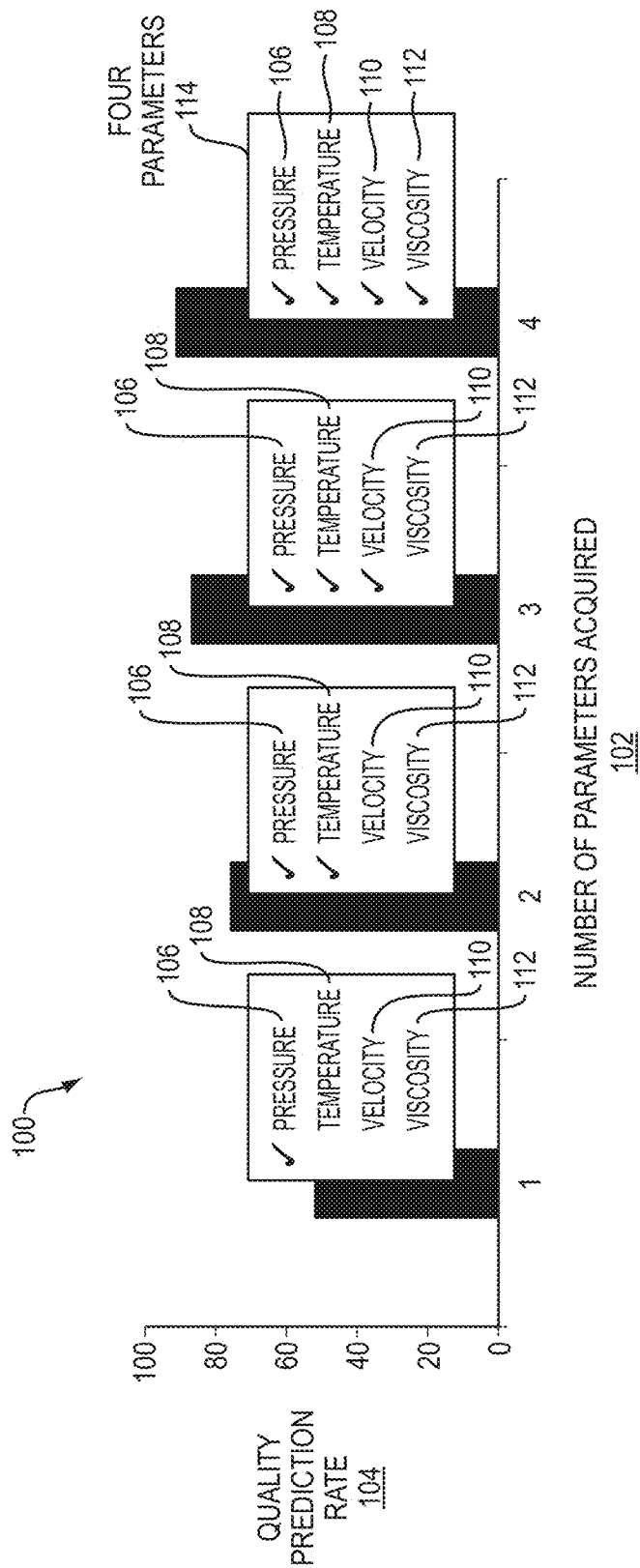
FIG. 1 is a diagram illustrating quality production rate as a function of four parameters observed in a manufacturing process.

A description of example embodiments of the invention follows.

One method for improving process control for quality assurance in injection molding is measuring of pressure, temperature, velocity (e.g. melt velocity or melt front velocity), and viscosity (e.g. melt viscosity or melt front viscosity) of a polymer melt within the injection mold online in real-time. An example of a polymer melt is a viscous compound. Accessing these four parameters during the manufacturing process can be difficult for manufacturers because it can require drilling holes in an existing injection mold or stamping die for installing wired sensors, which is expensive and sometimes prohibited by the complex internal structures, such as cooling lines and ejector pins. These issues realistically limit the number of sensors that can be integrated into a machine, and consequently limit the information that can be acquired for controlling manufacturing process.

A multivariate sensor and corresponding method according to an example embodiment of the present invention can enable simultaneous determination of these four parameters in injection molding using one single sensor unit, module, or package. Employing a single sensor unit, as opposed to employing separate sensors to measure different physical parameters, is advantageous for system miniaturization and energy efficiency. Embodiments described herein address sensing polymer melt velocity based on the melt temperature measured by an Infrared (IR) sensing element integrated within the sensor package. Use of a model, such as the Stephan-Boltzmann model, establishes an analytical relationship between melt front velocity and the ramping rate of the IR detector voltage output. Melt front velocity can be determined within an error of ±0.25%, under a broad range of melt temperature and IR detector diameters.

Injection molding is a widely used mass-production manufacturing process to produce plastic parts. In each injection molding cycle, raw plastic materials are heated in a barrel and forced into a mold cavity by a motor-driven screw under high pressure (e.g., at least 100 MPa). Once in the mold cavity, the melt cools down until it solidifies. Four states of the plastic melt—pressure, temperature, velocity, and viscosity—can significantly affect the quality of the molded parts through the constitutive viscoelastic behavior of the polymer being processed. As a result, accurate measurement and control of these parameters are useful to prevent products from having defects, such as blistering (e.g., layered zones on the part surface due to high temperature of the melt), flow marks (e.g., wavy lines or patterns due to low melt velocity), or short shots (e.g., the plastic being molded does not reach all areas of the mold cavity before solidifying).

Traditionally, the status of a plastic melt inside a mold can be estimated from pressure and temperature measurements at external check points (e.g., on the screw motor, barrel, cooling water pump, nozzle, or mold clamp). Numerical models then simulate the behavior of plastic melt flow inside the cavity using the pressure and temperature measurements. Although a simulated model may estimate the relative change of temperature or viscosity of the melt flow, the simulated model does not accurately account for temporal variations of the four parameters due to the difference between the modeled and actual boundary conditions within a complex mold structure.

FIG. 1 is a diagram 100 illustrating quality production rate as a function of four parameters 114 observed in a manufacturing process. Part quality can be predicted under 60% of the time when measuring one parameter (e.g., pressure 106). Part quality can be predicted 76.8% of the time when two of the four parameters 114 can be predicted (e.g., pressure 106 and temperature 108). Part quality can be predicted over 80% of the time when three of the four parameters 114 can be predicted (e.g. pressure 106, temperature 108, and velocity 110). Last, part quality (represented by the length variation of a tensile bar specimen) can be predicted 92.5% of the time from the four parameters 114 (e.g., pressure 106, temperature 108, velocity 110, and viscosity 112).

Accessing fewer parameters in the injection molding process correlates with a lower rate in product quality prediction. As described above, access to two process parameters lowers part quality predictability to 76.8%. Therefore, observing additional process parameters improves automated process and quality control A dual-parameter sensor can simultaneously measure both pressure and temperature of the plastic melt in the mold cavity and send data to an external receiver through acoustic wireless communication. For example, to measure melt velocity, an ultrasound sensor can be attached to the outside surface of the mold and can send an acoustic pulse toward the polymer melt in the mold cavity through the mold steel. The amplitude of the acoustic pulses reflected by the interface between the mold steel and air (e.g., the unfilled cavity) is different from that reflected by the interface between mold steel and plastic because of the difference in material properties that affect the acoustic wave deflection. As a result, the location of the melt front can be calculated at the receiver's end by measuring the reflected acoustic wave amplitude. Melt velocity can also be detected using magnetic sensors, which detect the location of the melt front by measuring the magnetic field formed by a moving conductive flow. While both methods are non-invasive, the accuracy of ultrasound detection decreases as the mold thickness increases because of diffusion of acoustic wave. Also, many plastic materials are non-conductive and thus cannot be detected using magnetic sensors.

Strain gauges can also be integrated into injection molding that can extract both thermal and mechanical characteristics during manufacturing. A micromachined wireless pressure sensor can also employ a resonant inductor-capacitor (LC) circuit in a micro-electrical-mechanical system (MEMS) cavity to convert the pressure change into frequency shift in the output signal. The wireless sensor uses radio frequency (RF) for communication, and, thus, is limited in data transmission from within a metallic environment, such as an injection mold or a stamping die.

Figure 2A:
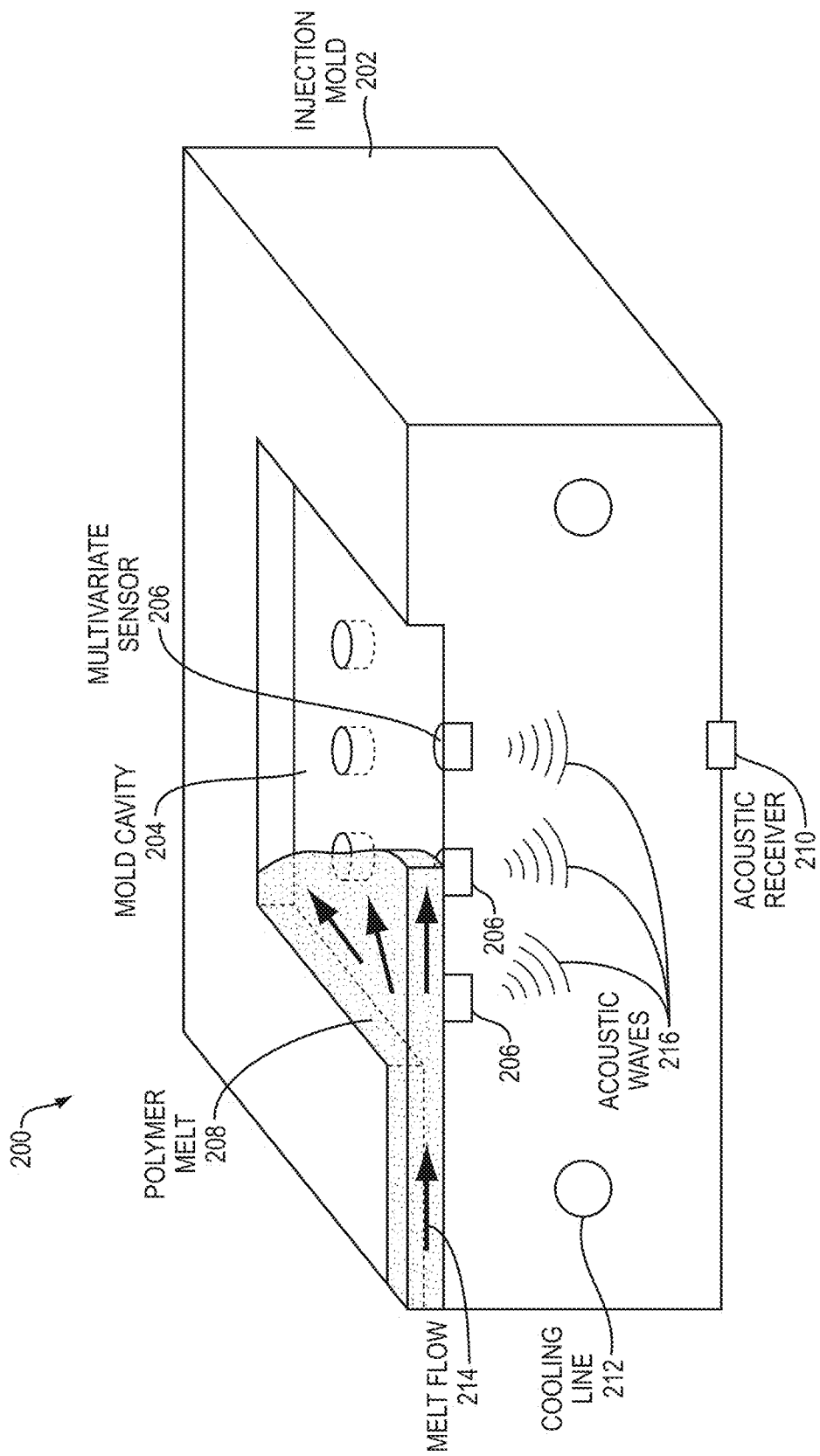
FIG. 2A is a block diagram illustrating an array of multivariate sensors embedded within a mold cavity, each of the multivariate sensors sensing four parameters.

FIG. 2A is a block diagram 200 illustrating an array of multivariate sensors 206 embedded within a mold cavity 204, each of the multivariate sensors 206 sensing the four parameters 114, as described above. A polymer melt 208 flows through a mold cavity 204 of an injection mold 202 such that the multivariate sensors 206 can detect a melt flow 214 using IR detectors and piezoelectric sensors. The multivariate sensors transmit measured data by means of acoustic waves 216 to at least one acoustic receiver 210 receivers outside of the injection mold 210. The injection mold 202 further has cooling lines 212 to perform cooling of the injection molding process.

Figure 2B:
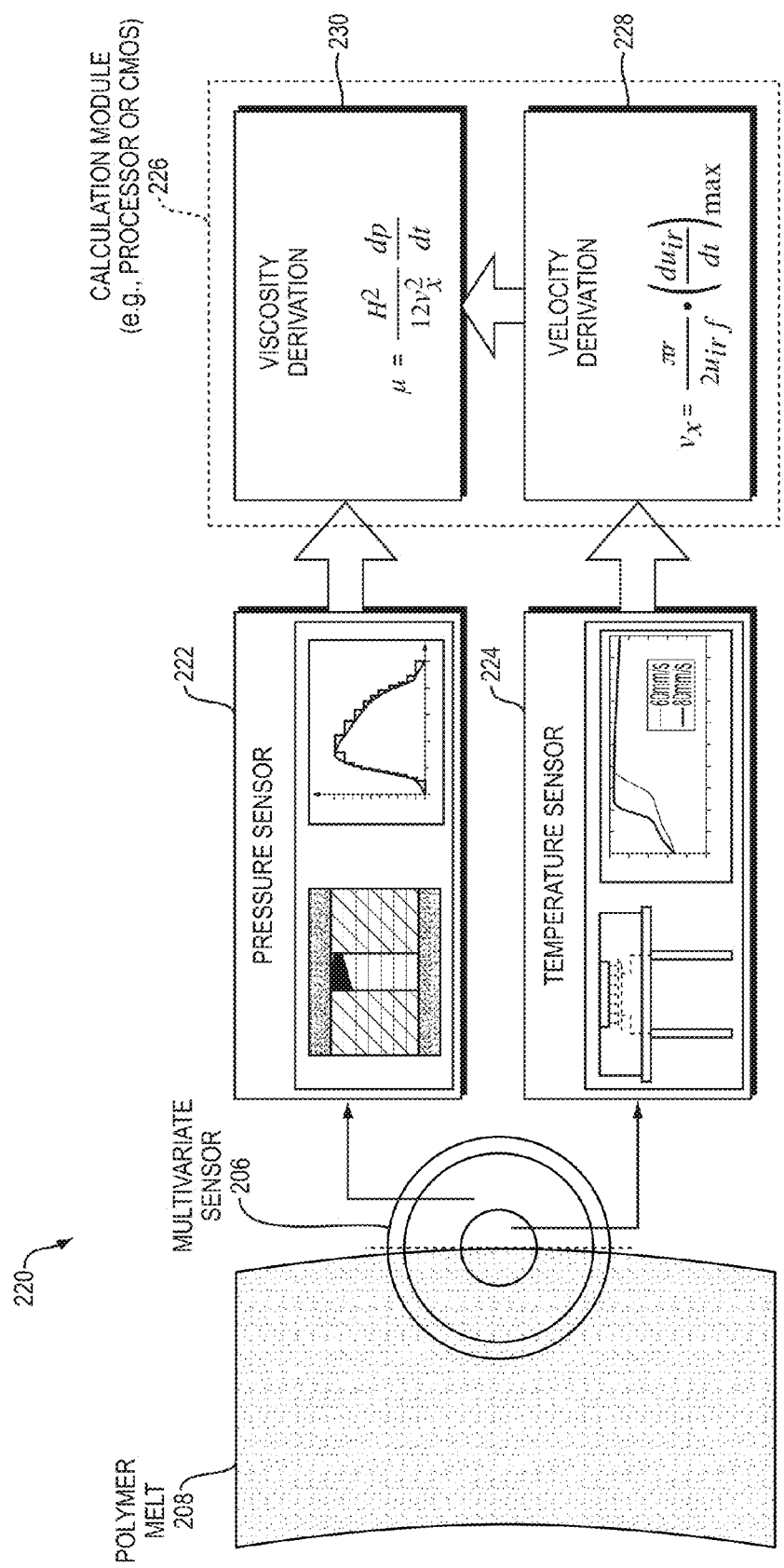
FIG. 2B is a block diagram illustrating an example embodiment of a multivariate sensor configured to calculate melt viscosity.

FIG. 2B is a block diagram 220 illustrating an example embodiment of the multivariate sensor configured to calculate melt viscosity. The multivariate sensor 206 includes a pressure sensor 222 that outputs a pressure reading and a temperature sensor 224 (e.g., an infrared detector) that outputs a temperature reading. A calculation module 226, for example a processor, CMOS, CMOS logic, or other hardware or software, calculates velocity 228 from the pressure and temperature readings. Optionally, the calculation module 226 calculates viscosity 230. Both velocity and viscosity can be calculated external to the injection mold, as well as in the calculation module 226 of the multivariate sensor. The calculation module 226 calculates melt velocity of the polymer melt 208 according to a melt temperature ramping rate and a time derivative of the melt pressure. Therefore, the multivariate sensor can detect melt pressure via its pressure sensor 222 (e.g., a piezoelectric stack). The multivariate sensor detects melt temperature using its temperature sensor 224, or IR detector, within the sensor package. The multivariate sensor can be configured such that the infrared detector is housed between (e.g., in the middle of) the piezoelectric stacks. Melt pressure excites the piezoelectric stacks and the charge generated by the stacks is proportional to the pressure. The IR detector takes advantage of the pyro-electric effect and generates charges in response to the radiating heat from the polymer melt, which is seen by the IR detector. Melt velocity can be calculated using the ramp rate of the melt temperature data, as measured by the IR detector. The IR director can capture the maximum ramp rate of the melt temperature variation because of the fast response time of the IR detector, which is on the order of 0.01 µs.

Figure 2C:
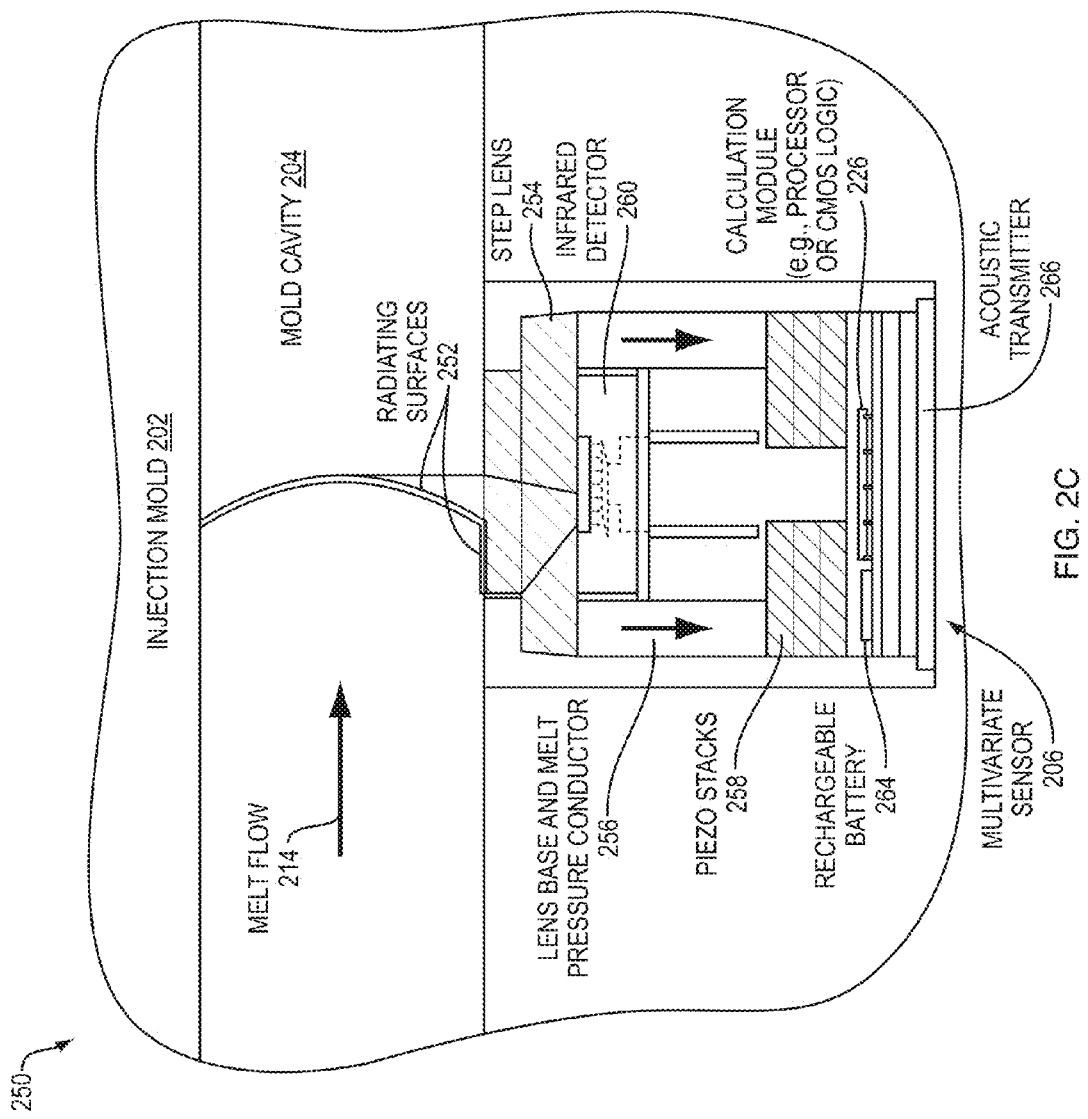
FIG. 2C is a block diagram illustrating an example embodiment of a configuration of a multivariate sensor.

FIG. 2C is a block diagram 250 illustrating an example embodiment of a configuration of a multivariate sensor structure. The multivariate sensor 206 is housed within the injection mold 202 under the mold cavity 204. In one embodiment, the multivariate sensor 206 includes a lens base and melt pressure conductor 256 coupled to a corresponding piezo stack 258, which detects pressure and charges a rechargeable battery 264. Further, a step lens 254 is disposed against an IR detector 260, which detects the temperature of the melt flow 214 by detecting the radiating surfaces 252.

FIG. 3A is a block diagram 300 illustrating an example embodiment of a multivariate sensor 206 equipped with the piezo stack 258 (e.g., a piezo-ceramic stack), the IR detector 260, the calculation module 226, and the acoustic transmitter 266. The piezo-ceramic stack 258 detects pressure variations of the melt flow 214 through the piezoelectric effect and additionally charges the rechargeable batter 264 to power the multivariate sensor 206. The IR detector 260 measures the melt temperature and front velocity. The calculation module 226 can calculate melt velocity from melt pressure and melt temperature. Either by an acoustic receiver or the calculation module 226 can calculate the melt viscosity from the three measured parameters (i.e., pressure, melt temperature, and melt front velocity) through polymer morphology.

A coded-acoustic wave modulation scheme enables the multivariate sensor 206 to transmit multiple parameters through an acoustic transmitter with variable gains. The coded-acoustic wave modulation enables selective resonant frequencies that provide the carriers for the individual parameters to be transmitted, while suppressing noise induced in the modulation process. Further, the coded-acoustic wave modulation scheme is applicable to a wide range of process monitoring scenarios.

An acoustic-based wireless sensor can be configured to measure and transmit multiple parameters from within one sensor package. Modulated acoustic waves can be employed as the medium for multivariate data transmission to enable data communication through an RF-shielded medium, as is commonly present in manufacturing machines. The acoustic-based wireless sensor can generate acoustic waves that carry process information through mechanical-electrical or electrical-mechanical conversion enabled by an acoustic transducer, and the acoustic waves can be received in the same manner. The acoustic-based wireless sensor includes an equivalent circuit model based on the KLM modeling to guide the structural design of the acoustic transducer for successful retrieval of multiple parameters remotely. The acoustic-based wireless sensor is designed to monitor four parameters that are useful to quality control in injection molding: melt pressure, temperature, velocity and viscosity, directly within the mold cavity, and transmit the measured signals wirelessly through acoustic waves, to a receiver outside of the mold, where no space limitation is present.

Figure 3B:
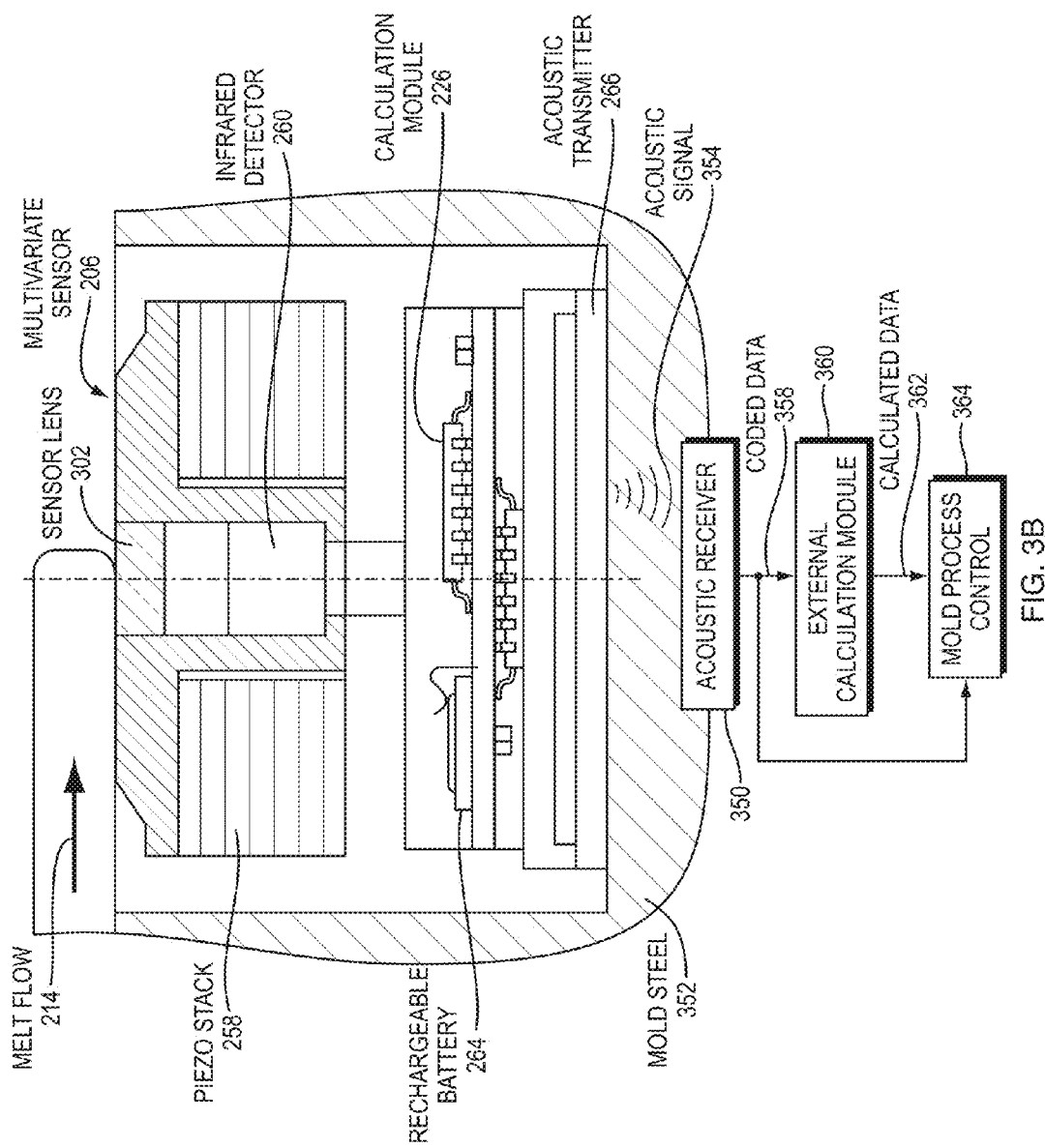
FIG. 3B is a block diagram illustrating an example embodiment of the multivariate sensor coupled to operatively communicate with an acoustic receiver.

FIG. 3B is a block diagram 350 illustrating an example embodiment of the multivariate sensor 206 coupled to operatively communicate with an acoustic receiver 356. FIG. 3B includes many elements of FIG. 3A, all of which are described similarly. However, in reference to FIG. 3B, the multivariate sensor 206 is embedded within mold steel 352. Therefore, the acoustic transmitter 266 transmits an acoustic signal 354 (e.g., pressure, temperature, and/or melt velocity) through the mold steel 352 to the acoustic receiver 356. The acoustic receiver filters the acoustic signal 354 to determine coded data (e.g., binary representations of pressure, temperature, and/or melt velocity). An external calculation module 360 then determines calculated data 362 (e.g., melt viscosity or melt velocity and melt viscosity). A mold process control module 364 then controls the injection molded process based on the coded data 358 and the calculated data 362.

The calculation module 226 can calculate melt velocity on the multivariate sensor 206. The calculation module 226 does so to save power, because transmitting the data for the external calculation module 360 to calculate melt velocity can consume more power. However, in an embodiment where providing power to the multivariate sensor 206 is easier, the calculation module 226 may allow the external calculation module 360 to calculate melt velocity. Similarly, the external calculation module 360 is configured to calculate melt viscosity because executing this calculation on the calculation module 226 can consume a lot of power. However, in an embodiment where providing power to the multivariate sensor 206 is easier, the calculation module 226 may calculate melt viscosity instead of the external calculation module 360.

Figure 4:
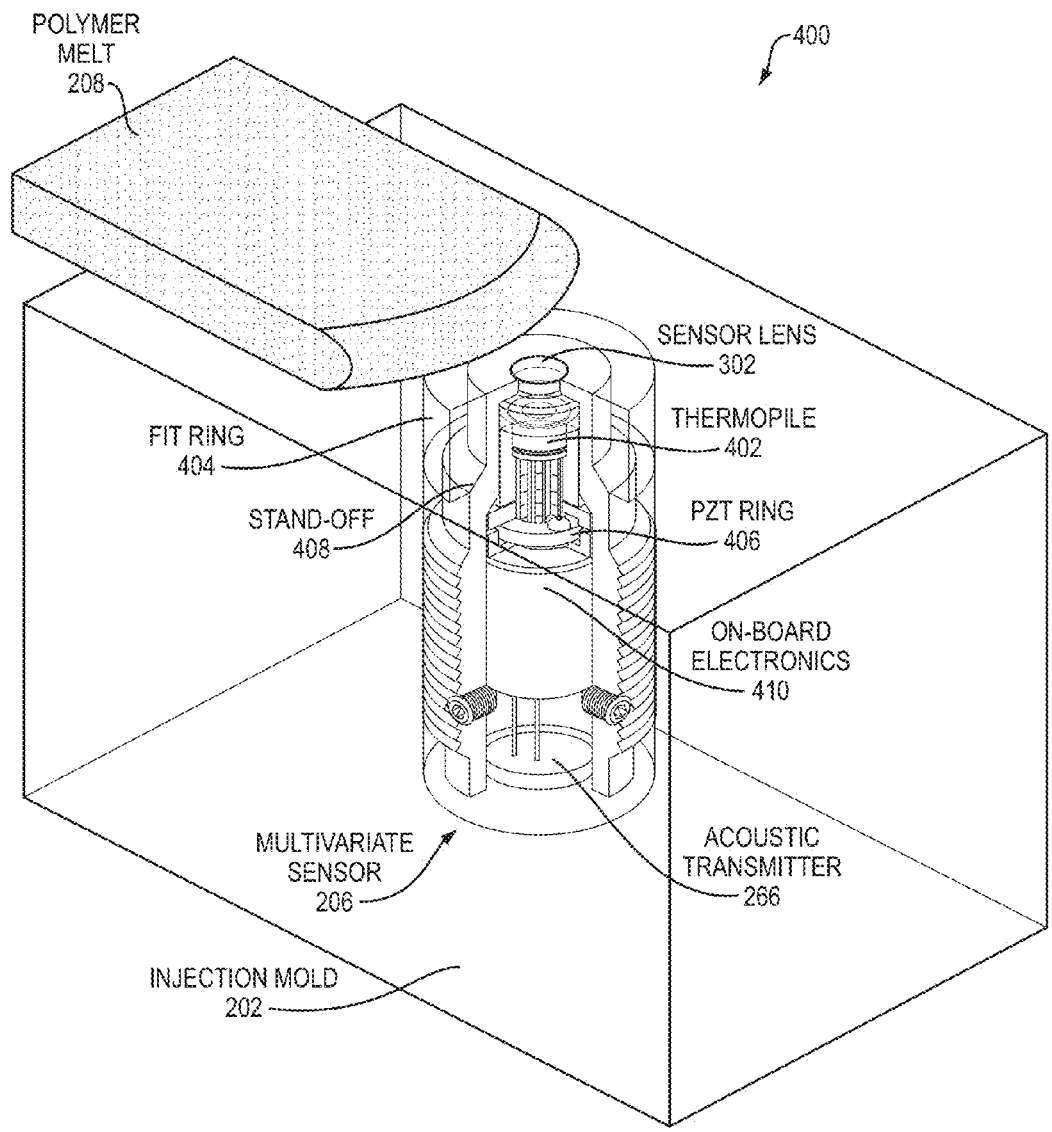
FIG. 4 is a block diagram illustrating the multivariate sensor including a piezo-ceramic stack, an infrared detector, and an acoustic transmitter.

FIG. 4 is a block diagram 400 illustrating the multivariate sensor 206 including a piezo-ceramic stack, an IR detector, and an acoustic transmitter 226. The piezo-ceramic stack takes advantage of the piezoelectric effect by converting the melt pressure into a proportional electrical charge output and providing a means for harvesting energy from the pressure differential associated with injection molding for powering the sensor electronics (in conjunction with a rechargeable battery, controlled by a hybrid powering algorithm). The IR detector takes advantage of the photovoltaic effect to generate a voltage signal upon exposure to thermal radiation in the IR region. The IR detector captures dynamics of the melt temperature profile. The IR detector has a fast response time on the order of 1 μs-$10^{-2}$ μs during the injection stage where the melt front moves over the sensor lens 302. The sensor lens 302 can include a lens or window that allows transmission of infrared radiation. The sensor lens can be constructed out of at least one of sapphire, germanium, zinc selenide, barium fluoride, or any other appropriate material. The multivariate sensor 206 further includes a fit ring 404 configured to fit the multivariate sensor 206 within the injection mold 202 by retaining the intended shape of the injection mold 202. Further, a stand-off module 408 holds the thermopile 402 (e.g., IR detector) coupled to its sensor lens 302 (e.g., a sapphire lens).

Figure 5A:
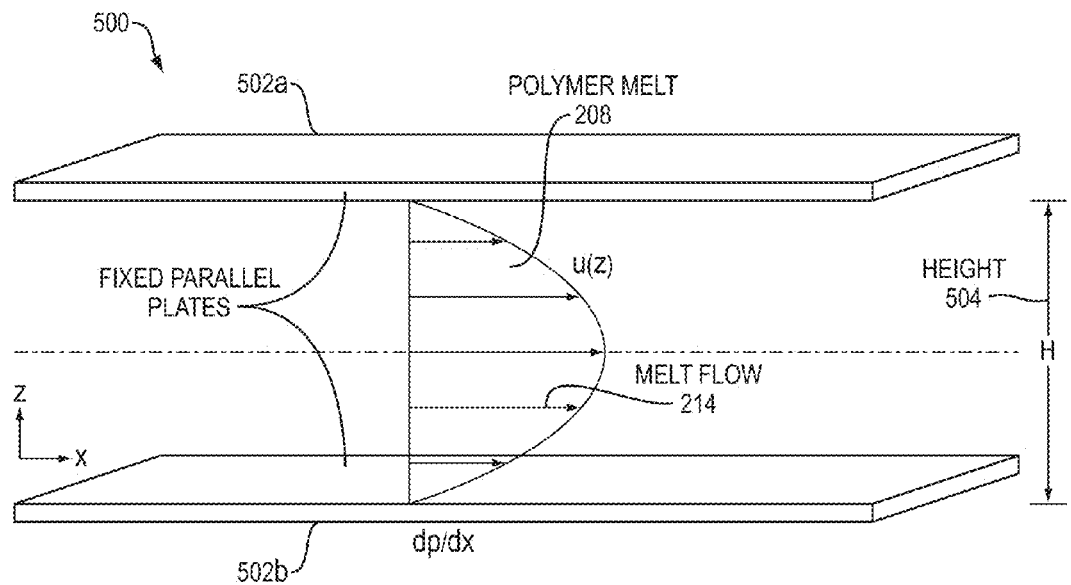
FIG. 5A is a block diagram illustrating melt flow between two fixed parallel plates.

FIG. 5A is a block diagram 500 illustrating melt flow 214 between two fixed parallel plates 502a-b, for example, of a mold. Melt flow 214 is a viscous flow between two fixed parallel plates. A rectangular cavity is assumed to calculate the melt viscosity. For a Newtonian and incompressible flow between two parallel plates at a distance of height 504 H from each other, the Navier-Stokes equation for the x direction gives:

$$\rho\left(\frac{du}{dt} + u\frac{du}{dx} + v\frac{du}{dy} + w\frac{du}{dz}\right) = -\frac{dp}{dx} + \rho g_x + \mu\left(\frac{d^2u}{d^2x} + \frac{d^2u}{d^2y} + \frac{d^2u}{d^2z}\right) \quad (1)$$

where μ is the viscosity. The equation can be solved in a two-dimensional space (d/dz=0) where v=w=0. From the continuity equation, the fluid velocity is seen as a function of z. Because of the incompressible fluid flow assumption, du/dx=0. Neglecting the gravitational force, the viscosity equation can be simplified as:

$$\frac{dP}{dx} = \mu\frac{d^2u}{dz^2} \quad (2)$$

The momentum equation in the z and y directions follows the same assumptions described above. The momentum equation leads to the pressure derivation equations with respect to y and z, and both are equal to zero. As a result, the pressure can be expressed as a function of x. Based on these results, the two quantities on both sides of Eq. (2) are independent from each other and equal to a constant. Applying the boundary conditions for Eq. (2), the final equation is expressed as:

$$\frac{dP}{dx} = \frac{12\mu v_x}{H^2} \quad (3)$$

where $v_x$ is the average velocity of the fluid across the z axis. From Eq. (3), fluid viscosity in a Lagrangian frame of reference can be determined when the pressure is monitored at least at two points along the flow direction. In such a viscosity inference method, the basics of Eulerian specification of flow field is considered, where fluid motion is considered for a specific location, as the fluid flows and time passes. Accordingly, the time derivative of the monitored pressure from a single sensor can be used as input for the viscosity calculation. The related equation can be derived by dividing both sides of Eq. (3) by a factor of dt, resulting in:

$$\mu = \frac{H^2}{12v_x^2} \frac{dP}{dt} \quad (4)$$

where dP/dt is the time derivation of the melt pressure as the melt passes the centerline of the sensor. Although the pressure sensor does not provide information on the point in time when the melt front passes the centerline of the sensor, the time when the melt passes the center line is same as the velocity sensor since these two sensors are sharing the same axial axis in the multivariate sensor structure.

The pressure measured by the pressure sensor is directly proportional to the voltage output of the sensor according to the following equation:

$$e = \frac{PAd_{33}}{C} \quad (5)$$

where $d_{33}$ is the charge constant of the piezoelectric material, e is the output voltage, A is the surface area of the sensor, and C is the capacitance of the capacitor in a charge amplifier circuit that converts the charge output from the piezoelectric to voltage. By taking the time derivative of the previous equation and considering that the only variables of the equation are P and u, dP/dt can be expressed as:

$$\frac{dP}{dt} = \frac{C}{d_{33}A} \frac{de}{dt} \quad (6)$$

The final equation presenting the relation for viscosity calculation is derived by substituting the left hand side of Eq. (6) into Eq. (4), yielding:

$$\mu = \frac{H^2 C}{12 v_x^2 A d_{33}} \frac{de}{dt} \quad (7)$$

where the parameters are as previously defined. In the next section, different fluid flow simulations are presented in a range of melt velocities and temperatures for evaluating the accuracy of the developed equation in calculating the melt viscosity.

Figure 5B:
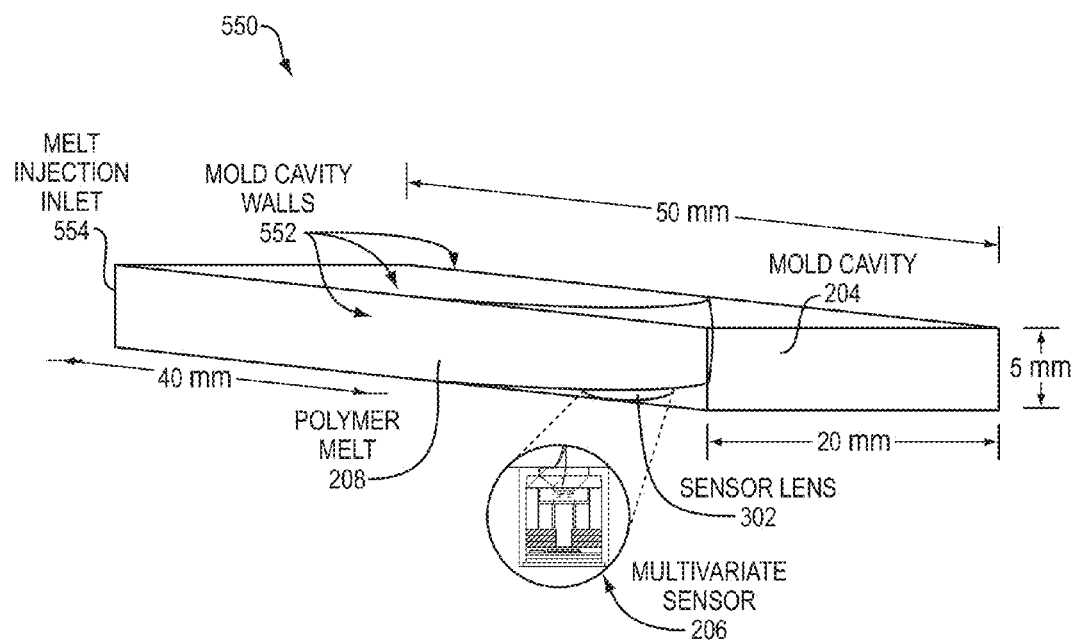
FIG. 5B is a block diagram illustrating an example embodiment of a cubic mold cavity.

FIG. 5B is a block diagram 550 illustrating an example embodiment of a cubic mold cavity 204. In this embodiment, the mold cavity 204 is modeled in the dimensions of 50 mm×20 mm×5 mm. Melt flow in the mold cavity 204 can be simulated on a COMSOL platform to numerically evaluate the developed equation for determining the melt viscosity. The initial and boundary conditions of the flow domain are defined accordingly. A constant flow rate of the flow is considered for the cavity inlet. The side edges of the mold cavity are considered as walls for boundary conditions. The fluid flow is considered as a Newtonian incompressible and isothermal flow. Fluid properties are considered the same as mechanical properties of propylene, where its density is 855 kg/m3 and its dynamic viscosity is set in the range of 100-1000 Pa·s, according to different inlet flow rate and temperature conditions.

Using the level set method for tracking the melt front interface, fluid flow is simulated during the filling phase of injection molding. When the melt flows over the multivariate sensor, the pressure of the melt excites the piezoelectric element, which causes the polarization of the piezoelectric crystals, which further causes the piezoelectric element to generate charge.

The piezoelectric stack is the basic element for converting energy. Generated charge from the piezoelectric stack can be calculated based on the equivalent force applied on the piezoelectric element. An amplifier circuit (e.g., an op-amp) is generally employed to convert the generated charge from the piezoelectric to voltage. The related voltage value, which is the output of the pressure sensor, is obtained by dividing the calculated charge by the capacitance of capacitor in the amplifier circuit. According to Eq. (5), generated charge is in direct relation with the $d_{33}$ coefficient which is equal to $4 \times 10^{-10}$ C/N, and inversely related to the capacitance of the capacitor in the amplifier circuit. According to the pressure range in common polymer injection molding process, which is 0 to 100 MPa, and using a capacitor with the capacitance value of 0.8 Nano-Farad, in the amplifier circuit, the output voltage range of the sensor will be in the range of 0 to 10 volt. For example when the melt crosses over the sensor centerline and its pressure is 1.25 MPa using the mentioned capacitor the output voltage would be about 4V.

FIG. 5C is a diagram 570 illustrating an example embodiment of output voltage 574 of the IR detector graphed over time for the melt to pass over a distance 572. In one embodiment, the output voltage ranges from approximately 0-10 Vs for a range of velocity from 120 to 180 mm/s, where the melt temperature is set to 206° C. Output voltage can vary for a range of melt velocities and viscosities in different temperatures. Simulation results show the output voltage in the time interval starts from when the melt comes over the sensor until it is completely covered by melt. The horizontal axis is normalized by the time value that it takes for the melt to pass over the sensor for the smallest velocity value to compare the results for different melt velocities. Therefore, the starting points for all the three cases are set to the origin of the diagram. The end points time is normalized proportionally. As the ramp rate of the output voltage increases, the melt velocity is increased but the viscosity depends on the time derivative of the output voltage and the melt velocity itself.

FIG. 6 is a diagram 600 of the polymer melt 208 moving over the sensor lens 302 (e.g., a sapphire lens) of the IR detector. Given that the output of the IR detector is proportional to the sensing area being exposed to the heat source, variation of temperature can be expressed as a function of the melt front location x and melt velocity $v_x$:

$$\frac{dT}{dt} = \frac{2r}{S_0} \cdot T_0 \sqrt{1 - \left(1 - \frac{x}{r}\right)^2} v_x \quad (1)$$

where $T_0$ is the melt temperature, and $S_0$ and r are the footprint area 206 and radius of the IR sensor lens, respectively. Mathematically, the maximum temperature ramping rate occurs when the melt front crosses the middle of the sapphire lens at point 1 612, where x=r, where x represents the distance from the start of lens 608. Thus, the melt velocity can be determined as a linear function of the maximum temperature ramping rate:

$$v_x = \frac{S_0}{T_0 \cdot 2r} \cdot \left(\frac{dT}{dt}\right)_{max} \quad (2)$$

With the melt velocity and pressure known, the melt viscosity, μ, can be inferred based on its definition:

$$\frac{dP}{dx} = \frac{12\mu v_x}{H^2} \rightarrow \mu = \frac{H^2}{12 v_x^2} \frac{dP}{dt} \quad (3)$$

where H is the known thickness of the mold cavity, v and dP/dt are the melt velocity and pressure, acquired by the multivariate sensor when the melt flow crosses the middle of the sensor.

The x-axis is represented by the horizontal line going across the center of the sensor along the melt flow direction. The point where the x-axis intersects with the left boundary (e.g., start of lens 602) of the IR detector is defined as x=0. Based on the Stephan-Boltzmann law, heat power radiating from an object is proportional to the temperature of the object to the fourth power. This relationship may be expressed as:

$$\phi_s = \epsilon \sigma T^4 \quad (4)$$

where $\phi_s$ is the radiating power, ε is the emissivity factor of the melt, σ is the Stephan-Boltzmann constant, and T is the melt temperature. If the IR detector absorbs all of the radiation power, the electrical charge generated by the sensing element, q, due to the gyro-electric effect, may be expressed as:

$$q = \frac{p \cdot k \cdot \phi_s}{A_f \cdot \sqrt{G_T^2 + \omega^2 H_P^2}} A \quad (5)$$

where t is the time, p is the pyro-electric coefficient, k is the loss factor of the IR radiation due to attenuation along the radiation path, A is the effective radiating surface area of the plastic melt (as shown in FIG. 3), which is a function of time and $A_f$ is the surface of the fully covered lens, φ is the frequency of the infrared, and $H_p$, $G_T$, η are the thermal conductance, heat capacitance, and emissivity coefficient of the sensing element in the IR detector, respectively.

Figure 7:
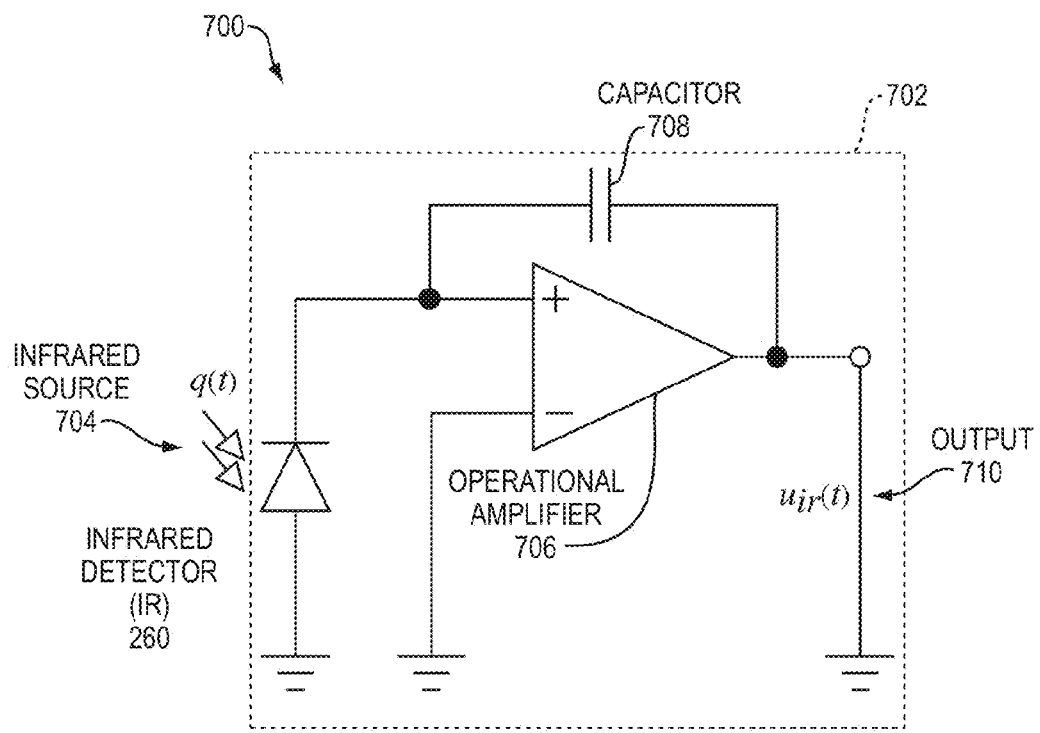
FIG. 7 is a circuit diagram illustrating an example embodiment of charge amplifier circuit employing an infrared detector.

FIG. 7 is a circuit diagram 700 illustrating an example embodiment of charge amplifier circuit 702 employing the IR detector 260. The charge amplifier circuit 702 includes the IR detector 260 employed to receive an IR source 704 (e.g., IR waves from the polymer melt), a capacitor 708, an operational amplifier 706 coupled with the capacitor 708, and an output port 710. Generally, a charge amplifier circuit 702 is employed to convert the output charge of IR detector 260 to a voltage output, in a manner expressed by:

$$u_{ir} = \frac{q}{C} = \frac{p \cdot k \cdot \phi_s}{C \cdot A_f \cdot \sqrt{G_T^2 + \omega^2 H_P^2}} A \quad (6)$$

where C is the feedback capacitance (e.g., of the capacitor 708) of the charge amplifier. The parameters p, φ, $H_p$, $G_T$, η, are constants determined by the pyro-electric material properties in the IR detector. Thus, the output voltage $U_{ir}$ is dependent only on the effective radiating surface area A. Considering the width of the mold cavity (typically wider than 20 mm) is generally multiples larger than the diameter of the IR detector (<6 mm), the radiation surface area or the area of lens exposed to the plastic melt, can be approximately expressed as a function of the melt front location x:

$$A = \frac{1}{2} r^2 2 \cos^{-1}\left(\frac{r-x}{r}\right) - (r-x)\sqrt{r^2 - (r-x)^2} \quad (7)$$

where r is the radius of the IR detector and the range of x is from 0 to 2r.

By taking the time derivative on both sides of the Eq. (3), the changing rate of output voltage $du_{ir}/dt$ can be expressed as:

$$\frac{du_{ir}}{dt} = \frac{p \cdot k \cdot \phi_s}{C \cdot A_f \cdot \sqrt{G_T^2 + \omega^2 H_P^2}} \cdot \frac{dA}{dx} \cdot v_x \quad (8)$$

where $v_x = dx/dt$ is the velocity of the plastic melt front. From Eq. (7), the derivative dA/dx has a maximum value when x=r. Assuming that the velocity $v_x$ is constant when the melt front flows through the IR detector, Eq. (8) can be rewritten as:

$$\left(\frac{du_{ir}}{dt}\right)_{max} = \frac{p \cdot k \cdot \phi_s}{C \cdot A_f \cdot \sqrt{G_T^2 + \omega^2 H_P^2}} \cdot 2r \cdot v_x \quad (9)$$

By substituting Eq. (6) into Eq. (9), the melt front velocity can expressed as:

$$v_x = \frac{\pi r}{2 u_{irf}} \cdot \left(\frac{du_{ir}}{dt}\right)_{max} \quad (10)$$

where $U_{irf}$ is the voltage output from the charge amplifier when the IR detector is fully covered by the plastic melt, as described in Eq. (6) when $A=A_f$. In realistic injection molding processes, the value of $u_{irf}$ and $(du_{ir}/dt)_{max}$ can be measured from the output voltage signal and its time derivative. Thus, the melt front velocity can be determined according to Eq. (10).

Figure 8:
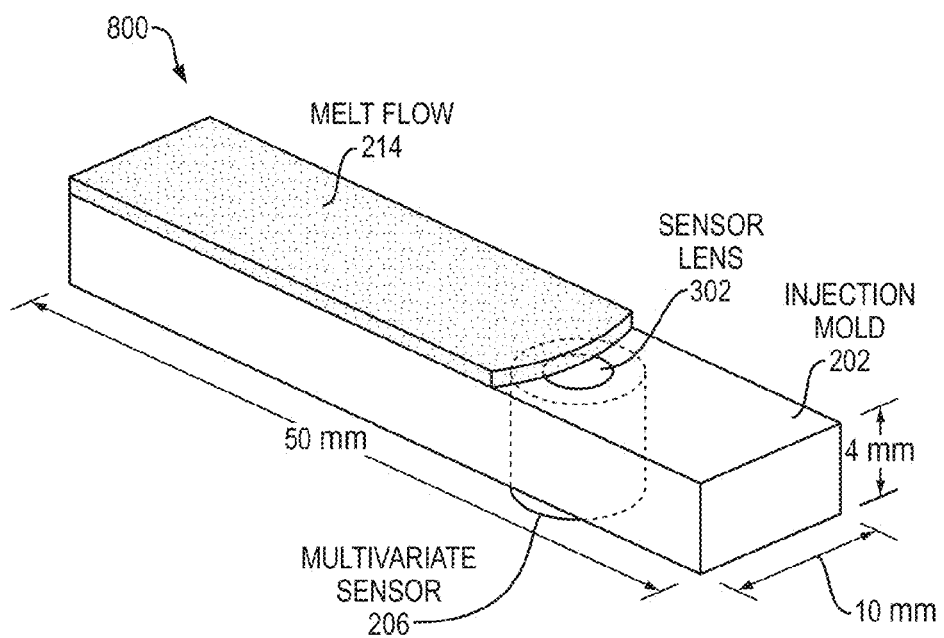
FIG. 8 is a diagram illustrating an example model of an injection mold embedded with a multivariate sensor.

FIG. 8 is a diagram 800 illustrating an example model of an injection mold 202 embedded with the multivariate sensor 206. The numerical model, built on the COMSOL platform, evaluates the new sensing method with consideration of the diffusion and attenuation of IR in the mold cavity. The numerical model is of a 50 mm×10 mm×4 mm injection mold embedded with the designed sensor. Free tetrahedral elements are employed for meshing the model. In the numerical model, the surface of the IR detector is meshed with higher density to ensure accuracy in quantifying the absorbed thermal energy by the FE elements of the IR detector. Parameters used for the simulation are listed in Table I, according to the realistic injection molding machine used for experimental study.

TABLE I

PARAMETERS SET IN SIMULATION

| | Thermal conductivity $(G_T)$ [W/(m · K)] | Heat capacitance $(H_p)$ [J/(kg · k)] | Emissivity factor ($\epsilon$) |
|---|---|---|---|
| Mold | 0.05 | 100 | 0.1 |
| IR detector | 93 | 840 | 0.99 |
| Polymer Melt | 10 | 900 | 0.99 |

Using the surface-to-surface radiation toolbox in COMSOL, radiation from the melt flow 214 to the IR detector and sensor package during the polymer filling stage can be simulated in a transient analysis, at a time step of 1.5 ms.

Figure 9A:
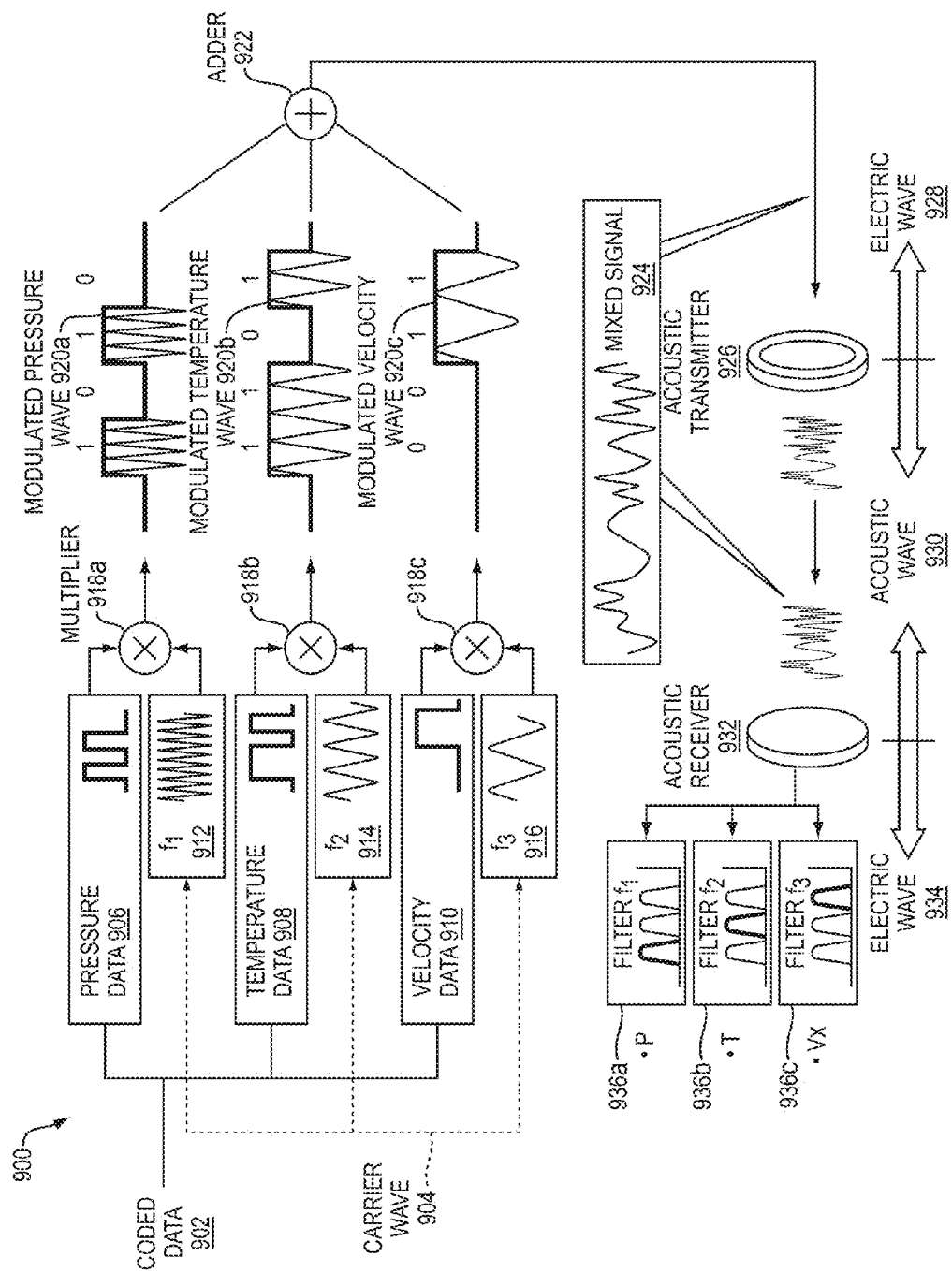
FIG. 9A is a signal diagram illustrating an example embodiment of creating an acoustic signal representing data detected by a multivariate sensor employing signal modulation, transmission, and demodulation.

FIG. 9A is a signal diagram 900 illustrating an example embodiment of creating an acoustic signal representing data detected by the multivariate sensor employing signal modulation, transmission, and demodulation. Each of the measured parameters is converted into a digital form of coded data 902 consisting of "1's" and "0's". For example, pressure data 906, temperature data 908 and velocity data 910 each are binary waves representing values measured by the multivariate sensor. Each of the coded parameters are then combined with a carrier wave 904 at a unique frequency (e.g., frequency 1 912, frequency 2 914, and frequency 3, 916) by way of a respective multiplier (e.g., multiplier 918a, multiplier 918b, and multiplier 918c). The multipliers output modulated pressure wave 920a, modulated temperature wave 920b, and modulated velocity wave 920c. The three waves 920 are summed by an adder 922 to create a mixed signal 924. The mixed signal 924 is transmitted to an acoustic transmitter 926 via an electric wave 928. The acoustic transmitter 926 emits a corresponding acoustic wave 930, for example, through the body of the injection mold. An acoustic receiver 932 on the other side of the injection mold receives the acoustic wave 930 and outputs a corresponding output electrical wave 934. The output electrical wave 934 is then filtered 936a-c to recover the coded data for pressure, temperature, and velocity.

Acoustic pulses are used as the information carrier to transmit the multiple measured parameters to a remote receiver outside of the metallic mold. A modulator then modulates the respective carrier frequencies (i.e., $f_1$, $f_2$, and $f_3$) by the digitized data.

Figure 9B:
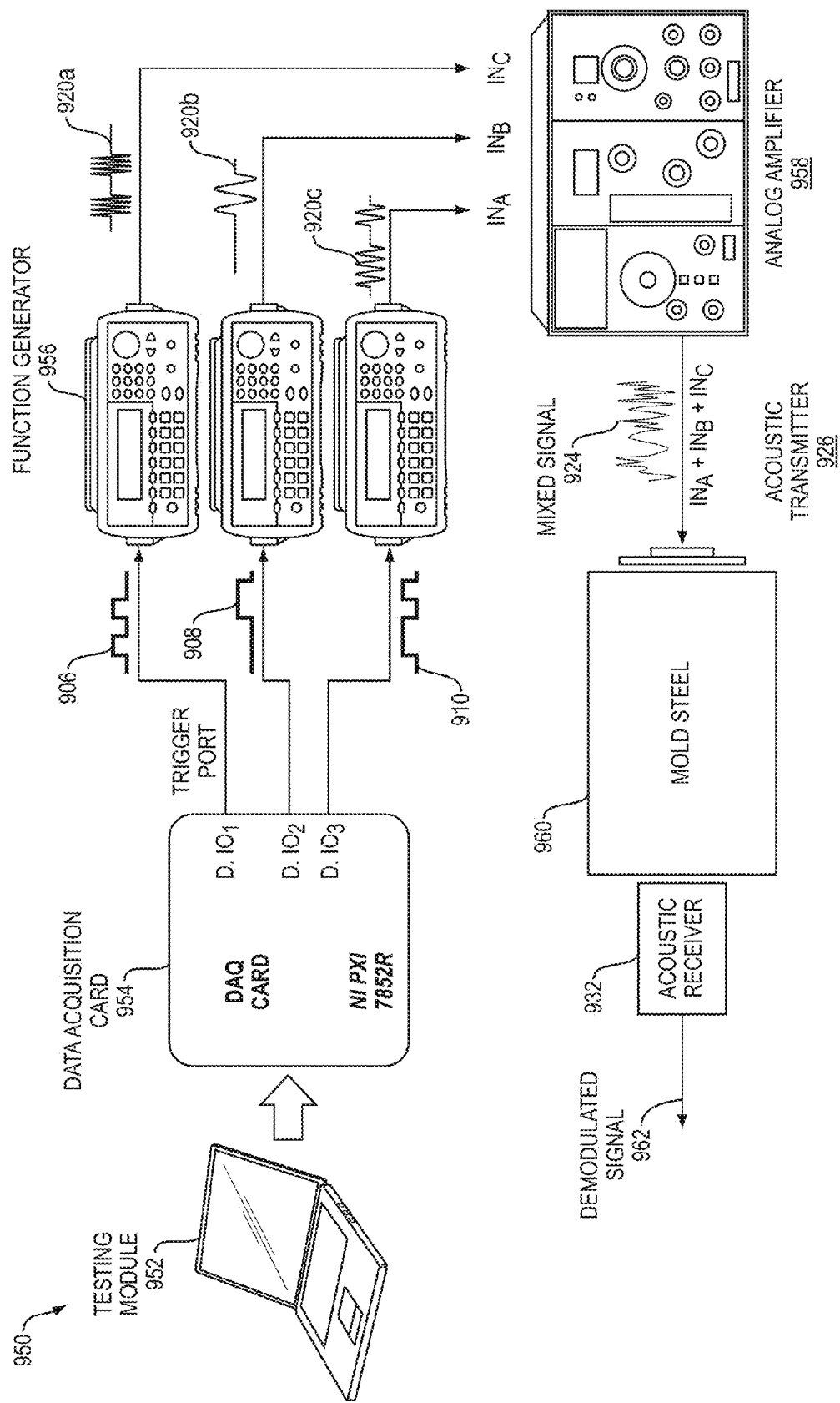
FIG. 9B is a block diagram illustrating a simulation environment to test the acoustic transmitter and acoustic receiver through a mold steel.

FIG. 9B is a block diagram 950 illustrating a simulation environment to test the acoustic transmitter 926 and acoustic receiver 932 through a mold steel 960. In one embodiment, a 40 mm thick mold steel 960 simulates an injection mold (not shown). The acoustic transmitter 926 and acoustic receiver 932 are located on the inside of the mold steel 960 and outside of the mold steel 960, respectively, representing the acoustic transmitter 926 and acoustic receiver 932 being on the inside of the injection mold (not shown) and outside of the injection mold (not shown). The acoustic transmitter 926 and acoustic receiver 932 can be placed opposite each other along the mold steal 960. A coupling layer of grease or wax can be between the acoustic transmitter 926 and acoustic receiver 932 and the mold steel 960, due to high acoustic impedance of air that reduces the efficiency of acoustic wave transmission.

A testing module 952 is coupled with a data acquisition card 954 (e.g. A 7852R DAQ card, which is an FPGA card has been implemented on PXI chassis and interfaced with LabVIEW). A processor of the testing module 952 executes a computer program to convert melt parameters (e.g., pressure, temperature, melt velocity, melt viscosity) into binary values and triggers the data acquisition care 954 to generate of the digital sine waves 906, 908, 910. Three function generators 956 (e.g., a 33250A Agilent function generator), generate the specific carrier frequencies (e.g., as sine waves). Each function generator 956 generates a continuous sine wave triggered by the digital sine waves 908, 910, 912 (e.g., according to the particular combination of digits representing the measured melt property such as temperature, pressure, or velocity in binary form). An analog amplifier 958 combines the signals together and generates one signal which includes all three signals 920a-c from the function generators 956. The simulation employs real time data acquisition because generation of the sine wave has to be triggered on the order of micro seconds.

Each channel is a combination of 8 digits. Two-hundred and fifty six tests (e.g., $2^8$ are executed to confirm that the data transmission is reliable for all of the possible combinations of the signal digits. However, some cases can be neglected because the signal is periodically generated. For example, for a signal with two digits, the signal has four different combinations. However, "01" is same as "10" when transmission is repeated and the total number of combinations would be equal to 3. The total number of required combinations to cover all the combinations of signal, avoiding from repeated tests is calculated as $2^{n-1}+1$, for a signal with n digits, which is equal to the total number of required tests. Therefore, for a signal with 8 digits there would be 129 combinations which can be covered in 43 tests since there are three channels available to transmit data. As an example, demodulation process has been done on a signal with the following combinations "10101011" and "11011010" and "11011001" for the three channels in order and results has been presented.

Figure 10A:
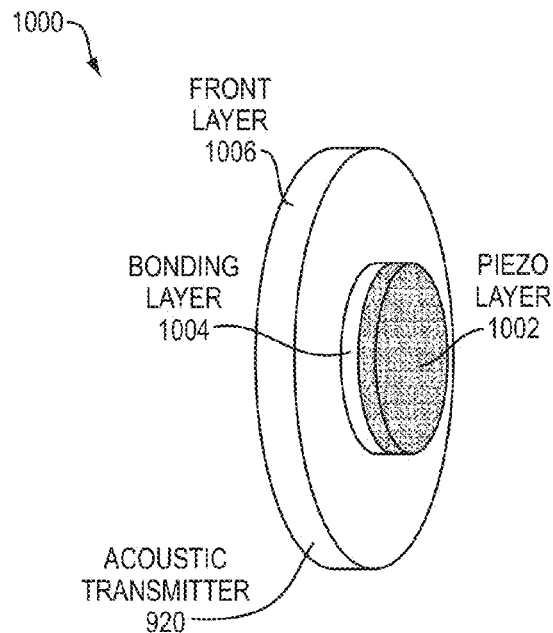
FIG. 10A is a block diagram illustrating an acoustic transmitter modeled as a three-layer structure.

FIG. 10A is a block diagram 1000 illustrating the acoustic transmitter modeled as a three-layer structure. A piezo layer 1002 converts electrical pulses generated by the piezo stack due to melt pressure variation and signaled at an electrical interface at the acoustic transmitter into acoustic pulses. A bonding layer 1004 is coupled to the piezo layer 1002 and a front layer 1006. The front layer 1006 is coupled to the bonding layer 1004 and the injection mold. Therefore, the acoustic transmitted is coupled with the injection mold through the bonding and front layers.

Figure 10B:
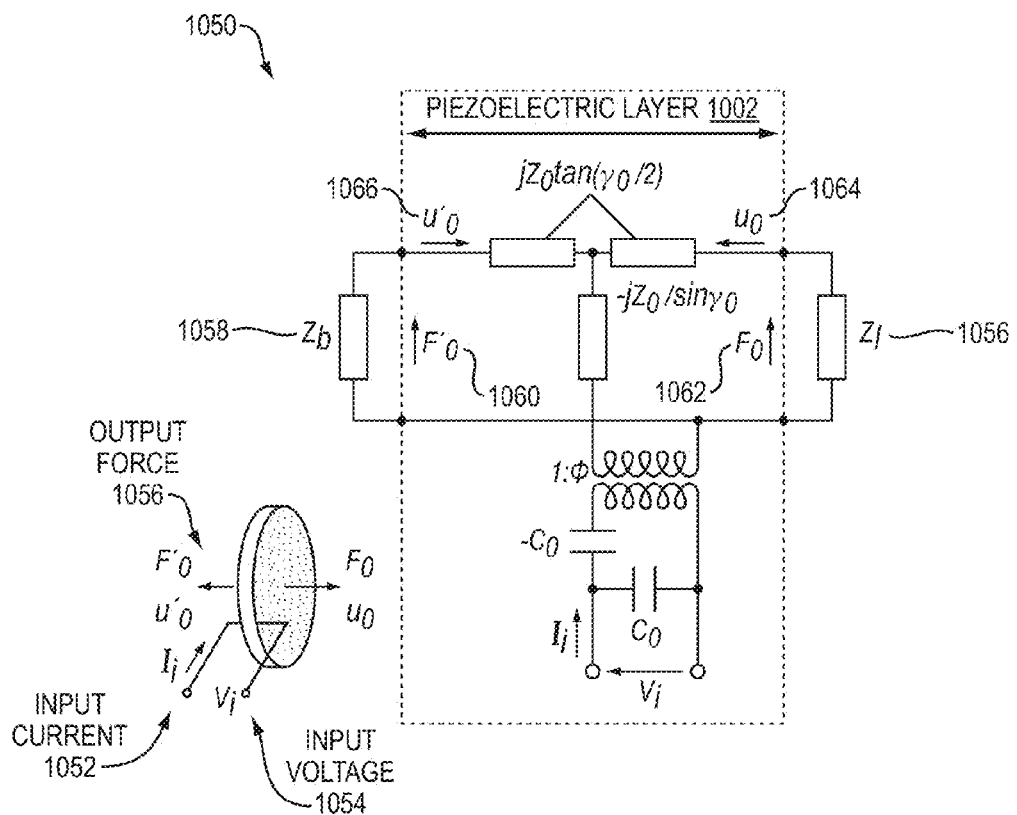
FIG. 10B is a circuit diagram of a piezo layer.

FIG. 10B is a circuit diagram of the piezo layer 1002 (e.g., piezoelectric layer 1002). Electrical impedance $Z_b$ 1058 and electrical impedance $Z_l$ 1056 represent the mechanical impedance of the materials in contact with the back and front surfaces of the piezo layer, respectively. The symbols $Z_0$, $\omega_0$, and $C_0$ represent the mechanical impedance, the resonant frequency, and the capacitance measured under zero strain in the piezo layer. The symbol $\gamma_0$ is the normalized frequency and $\phi$ is the ratio of the transformer, which characterizes the ratio of electrical and mechanical energy transformation. The output voltage and current associated with the impedance $Z_l$ are derived in terms of the input voltage $V_i$ 1054 and input current $I_i$ 1052, and applied to the piezo layer 1002.

The relationship is given in the matrix form as:

$$\begin{bmatrix} V_i \\ I_i \end{bmatrix} = \begin{bmatrix} A_0 & B_0 \\ C_0 & D_0 \end{bmatrix} \begin{bmatrix} F_0 \\ u_0 \end{bmatrix} \quad (4)$$

The transfer function of the piezo layer is therefore:

$$\begin{bmatrix} A_0 & B_0 \\ C_0 & D_0 \end{bmatrix} = \quad (5)$$

$$\frac{1}{\phi Q} \begin{bmatrix} 1 & j\phi^2/\omega C_0 \\ 0 & \phi^2 \end{bmatrix} \cdot \begin{bmatrix} \cos\gamma_0 + jz_b\sin\gamma_0 & Z_0(z_b\cos\gamma_0 + j\sin\gamma_0) \\ (j\sin\gamma_0)/Z_0 & 2(\cos\gamma_0 - 1) + jz_b\sin\gamma_0 \end{bmatrix}$$

Similar to the piezo layer 1002, the bonding layer 1004 and front layer 1006 of the transmitter are analyzed using the equivalent circuit models. The output voltage $F_n$ 1060, 1062 and current $u_n$ 1064, 1066 of the transmitter corresponding to the input voltage $F_{n-1}$ and current $u_{n-1}$ are represented in the matrix form as:

$$\begin{bmatrix} F_{n-1} \\ u_{n-1} \end{bmatrix} = \begin{bmatrix} A_n & B_n \\ C_n & D_n \end{bmatrix} \begin{bmatrix} F_n \\ u_n \end{bmatrix} \quad (6)$$

where the transformation matrix is given by:

$$\begin{bmatrix} A_n & B_n \\ C_n & D_n \end{bmatrix} = \begin{bmatrix} \cos\gamma_n & jZ_n\sin\gamma_n \\ (j\sin\gamma_n)/Z_n & \cos\gamma_n \end{bmatrix} n = 1, 2, 3, \text{ and } 4 \quad (11)$$

The frequency characteristic of the multi-layered transmitter is calculated by multiplying the matrices for the various layers to obtain a governing matrix that relates the excitation voltage Vi and current Ii (input to the piezo layer) to the sound force F3 and velocity u3 (output) of the mold steel:

$$\begin{bmatrix} V_i \\ I_i \end{bmatrix} = \begin{bmatrix} A_t & B_t \\ C_t & D_t \end{bmatrix} \begin{bmatrix} F_3 \\ u_3 \end{bmatrix}, \text{ where } \begin{bmatrix} A_t & B_t \\ C_t & D_t \end{bmatrix} = \prod_{n=0}^{3} \begin{bmatrix} A_n & B_n \\ C_n & D_n \end{bmatrix} \quad (7)$$

Through a reciprocal approach, the governing matrices for the acoustic receiver outside of the mold cavity are derived, where the input and output terms in Eq. (7) were interchanged such that the input for the receiver was the sound force $F_3$ and the output was the electrical voltage $V_o$. The final transfer function relating the input voltage $V_i$ to the piezo layer and the output voltage $V_o$ converted by the ultrasound receiver is represented as:

$$\frac{V_o}{V_i} = \frac{2R_l Z_{0t}}{[A_t Z_{0t} + B_t + Z_s(C_t Z_{0t} + D_t)][A_r Z_{0t} + B_r + Z_l(C_r Z_{0t} + D_r)]} \quad (8)$$

where $Z_l = R_l + fX_{si}$ is the electrical impedance of the voltage measuring instrument connected to the ultrasound receiver, $Z_{0t}$ is the mechanical impedance of the mold steel, and $Z_s = R_s + jX_s$ represents the electrical impedance of the signal generation source that excites the transmitter.

Figure 11:
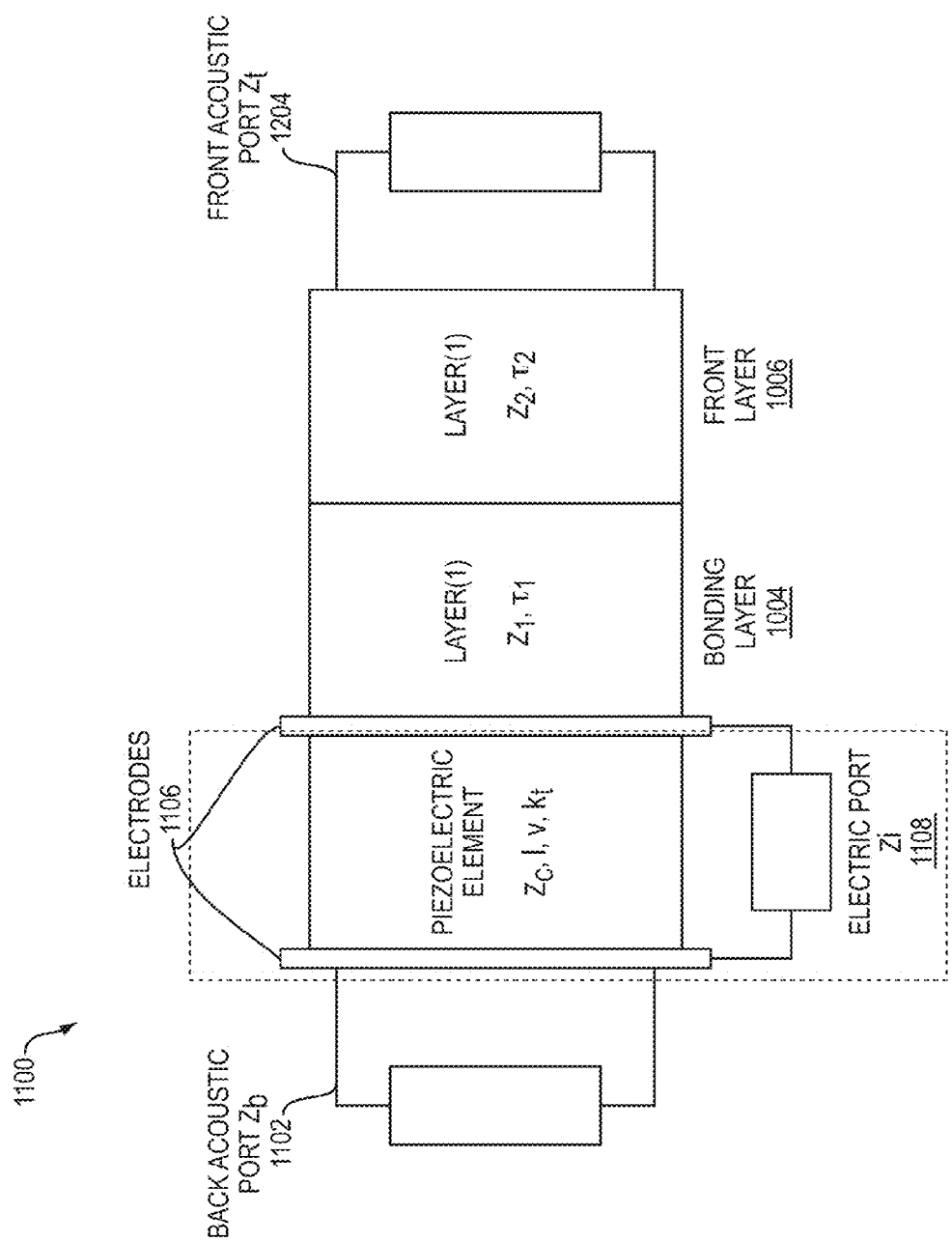
FIG. 11 is a block diagram illustrating an example embodiment of an acoustic transmitter employing a three-layer structure.

FIG. 11 is a block diagram 1100 illustrating an example embodiment of an acoustic transmitter employing a three-layer structure. The acoustic transmitter employs a piezo layer 1002, a bonding layer 1004, and a front layer 1006. The piezo layer 1002 is coupled to electrodes 1106, which receive an input from an Electric port 1108. The piezo layer 1002 receives an impedance from a back acoustic port 1102. The front acoustic port 1104 receives an impedance from a front acoustic port 1104. The acoustic transmitter can be represented by a KLM equivalent circuit, where each layer of the acoustic transmitter is modeled as a two-port network that enables the conversion of electrical variables (e.g., voltage V and current I) to mechanical variables (e.g., force F and velocity u) or vice versa (e.g., in the case of an acoustic receiver).

Figure 12A:
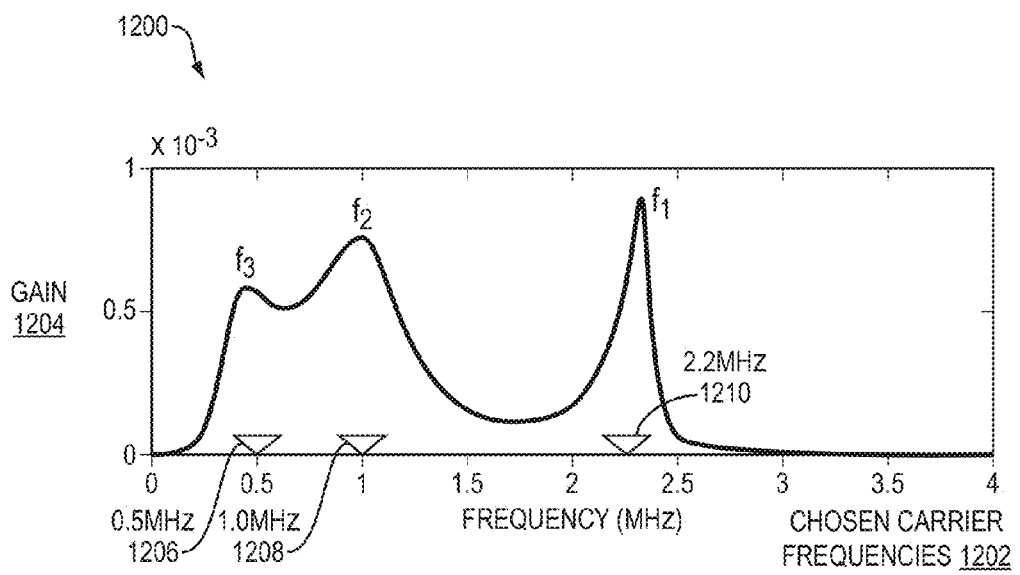
FIG. 12A is a chart diagram illustrating an example embodiment of gain for chosen carrier frequencies.

FIG. 12A is a chart diagram 1200 illustrating an example embodiment of gain 1204 for chosen carrier frequencies 1202. The chosen carrier frequencies 1202, in this embodiment, are a first carrier frequency 1206 0.5 MHZ, a second carrier frequency 1208 1.0 MHz, and a third carrier frequency 1210 2.2 MHz. The gain of the modeled acoustic transmission system is calculated by applying an impulse input to the piezo layer, which is consistent with the mode of sensor operation. Frequency bands of high gains quantify carrier frequencies to transmit multiple process parameters. In the embodiment illustrated in FIG. 12A, the thickness of the front layer, bonding layer, and piezo layer are 0.7 mm, 0.1 mm, and 1.0 mm, respectively.

The impedance of $Z_b$ and $Z_l$ were 10Ω and 100 MΩ, respectively, based on representative specifications provided by ultrasound transducer manufacturers. Particular resonance frequencies can be adjusted by varying the thickness of the piezo, front, and bonding layers, resonant frequencies of the three-layered transmitter. When the carrier frequency of the input signal matches the natural frequencies, a maximal signal amplitude and SNR on the receiver's side is received. The three peaks at 0.5, 1.0, and 2.2 MHz correspond to the resonant frequency of the acoustic transmitter at the first, second, and third mode of vibration, respectively. Accordingly, the carrier frequencies for transmitting the pressure, temperature, and velocity data are 0.5 (Channel 3), 1.0 (Channel 2), and 2.2 MHz (Channel 1), respectively.

Upon reception, a receiver demodulates the transmitted signal through wavelet transform for parameter extraction. For reliable wireless data transmission through multiple channels, the multivariate sensor provides a signal with a high gain for frequency components that serve as the carrier frequencies for high signal-to-noise ratio (SNR) parameter modulation. At the same time, the sensor has a low gain for other frequency components to minimize signal interference.

Figure 12B:
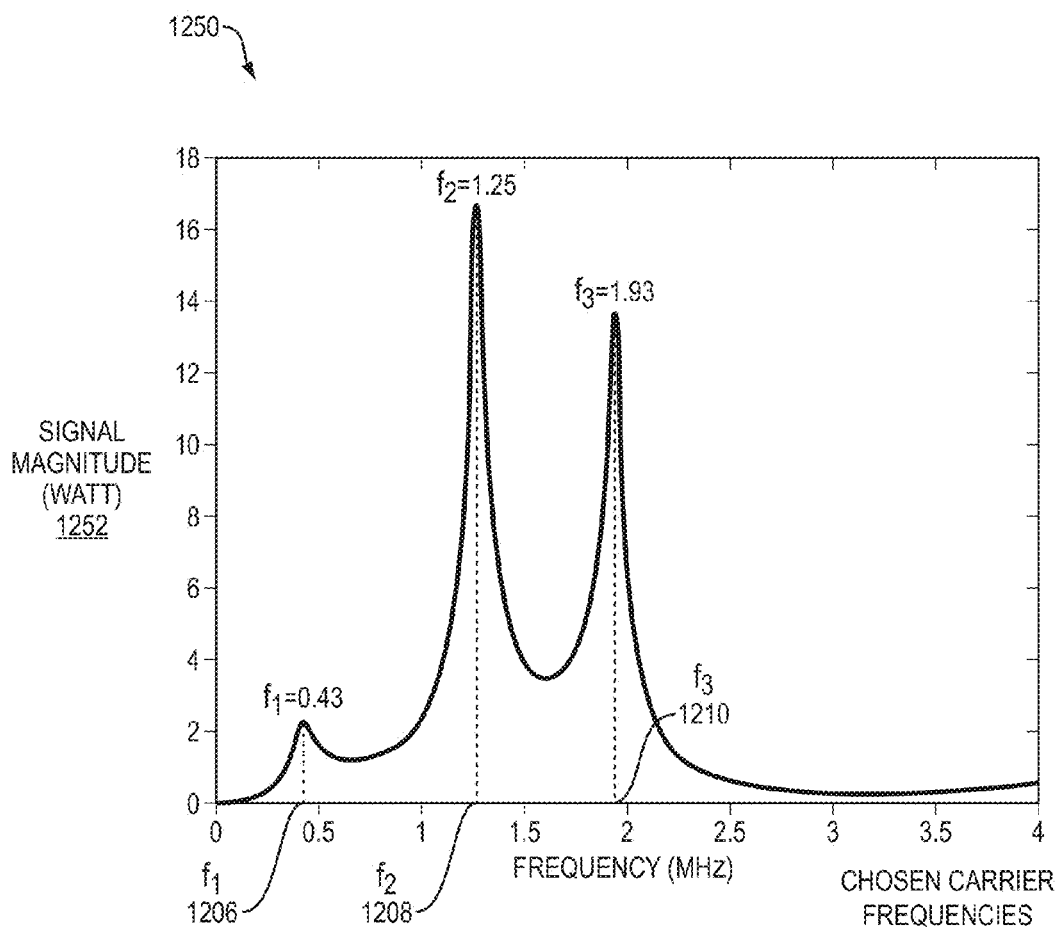
FIG. 12B is a graph diagram illustrating another example embodiment of signal magnitudes for various carrier frequencies.

FIG. 12B is a graph diagram 1250 illustrating another example embodiment of signal magnitudes 1252 for various carrier frequencies 1202. In this example, the thickness of the front layer, bonding layer, and piezo layer are 0.7 mm, 0.1 mm, and 1.0 mm, respectively. By varying the thickness of the front layer, bonding layer, and piezo layer, resonant frequencies of the three-layered transmitter can be achieved according to Eq. (16-17).

Figure 13A:
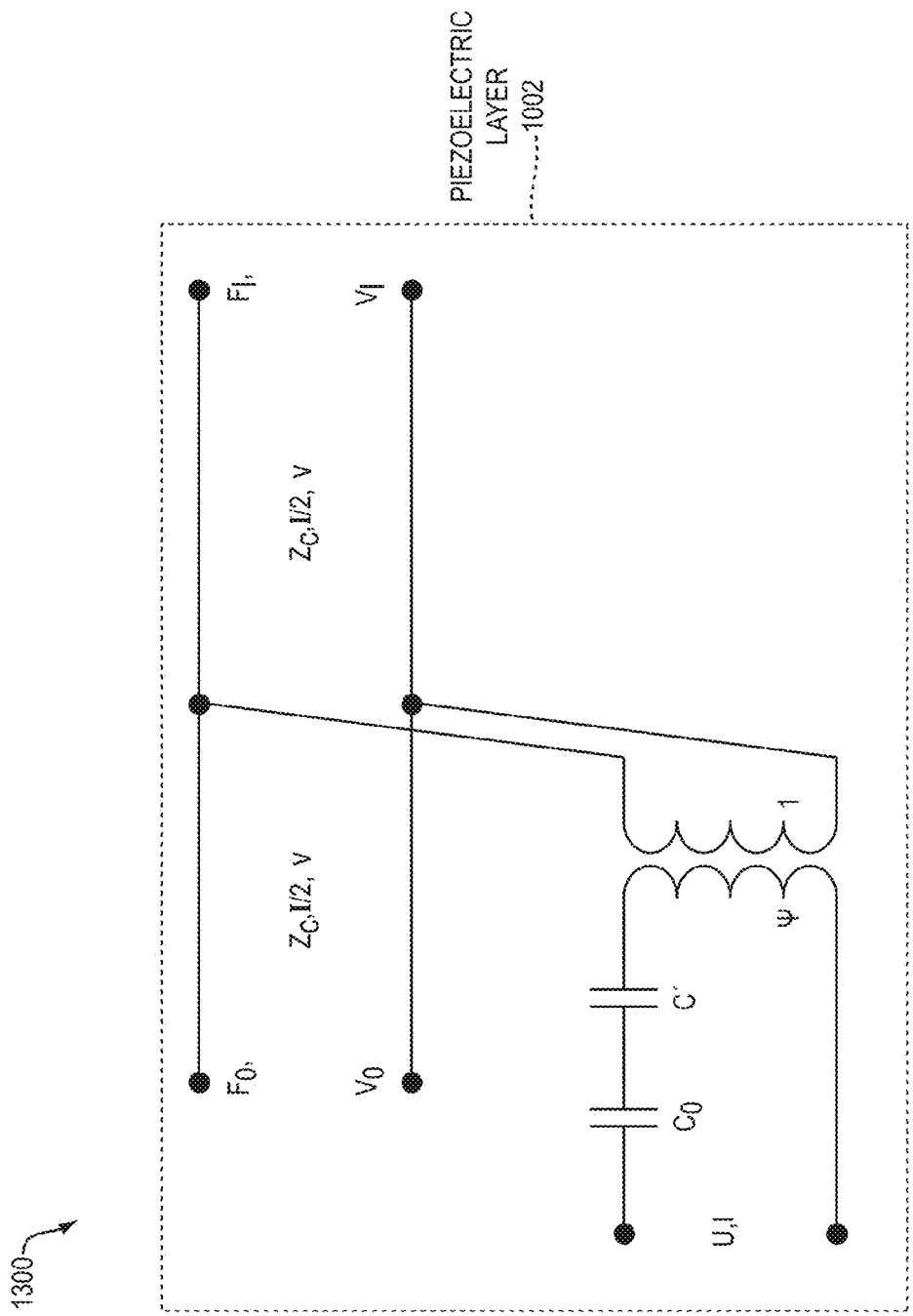
FIG. 13A is a circuit diagram illustrating an example embodiment of a piezo layer employed in the acoustic transmitter.

FIG. 13A is a circuit diagram 1300 illustrating an example embodiment of the piezo layer 1002 employed in the acoustic transmitter. The electrical impedances $Z_b$ and $Z_t$ represent the mechanical impedance of the materials in contact with the back and front surfaces of the piezo layer 1002, respectively. The symbols $Z_c$, l, v, and k represent the mechanical impedance, the thickness, the sound velocity, and the coupling factor measured under zero strain in the piezo layer 1002, respectively. The piezo layer 1002 converts electrical pulses generated by the piezo layer 1002 as a result of the melt pressure into acoustic pulses. Through the bonding and front layers, the transmitter is coupled with the mold structure. The circuit introduces a transfer function to relate the transmitted and incident voltage potential in Laplace domain.

$$H(p) = \frac{2Z_t}{-Z_iZ_tn_{21} + Z_in_{11} + Z_tn_{22} - n_{12}} \quad (4)$$

where, $p=j\omega$ is the imaginary frequency ($\omega$ is the frequency).

Figure 13B:
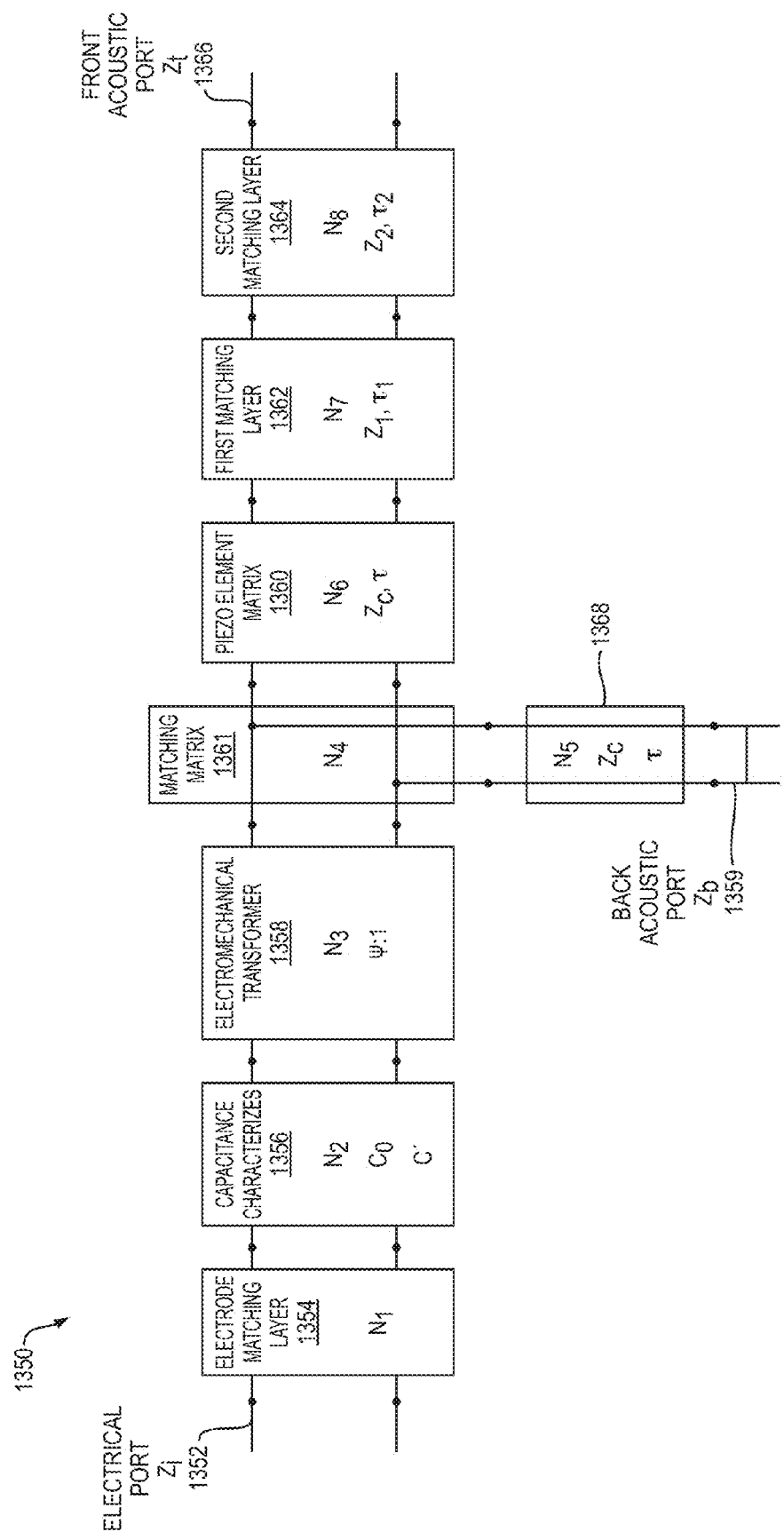
FIG. 13B is a block diagram illustrating an example embodiment of a transducer employed in an acoustic transmitter.

FIG. 13B is a block diagram 1350 illustrating an example embodiment of a transducer employed in the acoustic transmitter. The three layers of the acoustic transmitter are participating in the final N matrices. Matrix $N_1$ represents an electrode matching layer 1354 and is an electrical coupling transmitter matrix which is a function of n as a transformer and a serial inductance L because the matrix components are selected after the solution of the scheme this matrix is eliminated. Matrix N1 receives input from electrical port 1352.

$$N_1 = \begin{pmatrix} n & -\frac{pL}{n} \\ 0 & \frac{1}{n} \end{pmatrix} \quad (5)$$

The capacitance characteristics matrix 1356 is represented by N2:

$$N_2 = \begin{pmatrix} 1 & -\frac{C_0 + C'}{pC_0C'} \\ 0 & 1 \end{pmatrix} \quad (6)$$

where, $C_0 = \epsilon^s A/l$ and A is the surface area of the transducer, l is the thickness of the piezoelectric element, $\epsilon^s$ is the electrical permittivity at constant strain, $K_t$ is the coupling factor, and the resonance frequency is $\omega_0 = \pi v/l$. Matrix C' can be expressed as:

$$C' = \frac{C_0}{K_t^2 \text{sinc}(\omega/2\omega_0)} \quad (7)$$

The $N_3$ matrix represents an electromechanical transformer 1358 and introduces electromechanical properties:

$$N_3 = \begin{pmatrix} \frac{1}{\psi} & 0 \\ 0 & \psi \end{pmatrix} \quad (8)$$

where parameter $\Psi$ can be expressed as:

$$\psi = K_t \sqrt{\frac{\pi}{\omega_0 C_0 Z_C}} \text{sinc}(\omega/2\omega_0) \quad (9)$$

The $N_4$ matrix is the matching matrix 1361 between the backing and the piezoelectric element:

$$N_4 = \begin{pmatrix} 1 & 0 \\ -\frac{1}{Z_L} & 1 \end{pmatrix}, \quad (10)$$

where, $Z_L$ is the net impedance expressed as a function of the $\tau=1/2v$.

$$Z_L = Z_C \frac{Z_C \sinh(p\tau) + Z_b \cosh(p\tau)}{Z_C \cosh(p\tau) + Z_b \sinh(p\tau)} \quad (11)$$

The electromechanical matrix 1368 can be calculated by matrix multiplication of the last four mentioned matrices. $N_5$ represents the half of the piezoelectric element which is modeled as the transmission line.

$$N_5 = \begin{pmatrix} \cosh(p\tau) & -Z_C \sinh(p\tau) \\ -\frac{1}{Z_C} \sinh(p\tau) & \cosh(p\tau) \end{pmatrix} \quad (12)$$

$N_6$, or piezo element matrix 1360, represents half of the transducer related to front end which would be similar as $N_5$ and the transducer front end layers can be modeled as transmission lines where the only difference in related matrixes would be the velocity and the thickness of the matching layers which defines the propagation times $\tau_1$, $\tau_2$.

$$N_6 = \begin{pmatrix} \cosh(p\tau_1) & -Z_1 \sinh(p\tau_1) \\ -\frac{1}{Z_1} \sinh(p\tau_1) & \cosh(p\tau_1) \end{pmatrix} \quad (13)$$

The total matrix which contains all the n layers of the transducer is calculated as:

$$N_t = \prod_{j=1}^{n} N_{n-j+1} \quad (14)$$

Assuming that the excitation signal to the transducer is a unit impulse which means $U(\omega)=1$ in the Laplace domain, the frequency response function of the transducer can be expressed as:

$$H_t(p) = \frac{2Z_t}{-Z_E Z_t N_{t21} + Z_E N_{t11} + Z_t N_{t22} - N_{t12}} \quad (16)$$

where, $H_t(p)$ is the transmission transfer function and $Z_E$ is called the electric supply resistance.

$$Z_E = \frac{Z_t N_{t22} - N_{t12}}{N_{t11} - Z_t N_{t21}} \quad (17)$$

The gain of the modeled acoustic transmission system is calculated by applying an impulse input to the piezo layer, which is consistent with the mode of sensor operation. Frequency bands of high gains are identified for quantifying carrier frequencies to transmit multiple process parameters.

Figure 14:
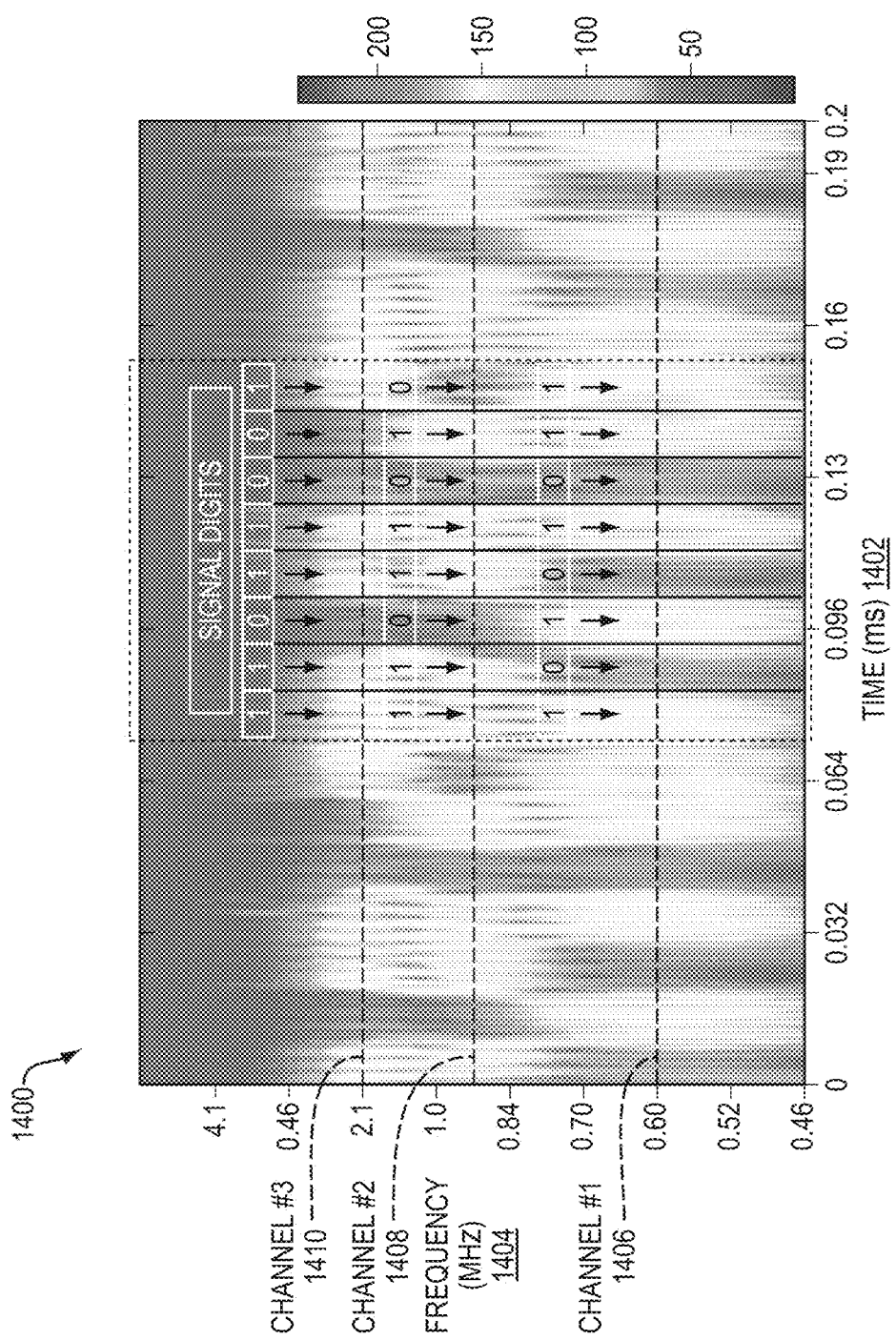
FIG. 14 is a graph diagram illustrating an example embodiment of a received signal before a demodulation process.

FIG. 14 is a graph diagram 1400 illustrating an example embodiment of a received signal before demodulation process. An oscilloscope (e.g., a Tektronix MSO3012 oscilloscope) can sample the signal. The sampling rate is approximately 625e8 per seconds while a period of 20 microseconds of the signal is sampled for each test. The signal is '1' for each channel where the signal is mostly present in the middle of the channel's frequencies. The signal is '0' for each channel where the signal is mostly not present in the middle of the channel's frequencies. A Morlet Wavelet Transform can demodulate the received signal.

FIG. 15A is a diagram 1500 illustrating different WT coefficients 1504 for center frequencies of each channel. The WT coefficients 1504 for each channel 1406, 1408, 1410 can be used to convert the results from the WT into a step signal that presents the detected "1" and "0" digits clearly. The absolute values of a Hilbert transform of the WT coefficients are calculated to envelope the signal to eliminate the periodic property of the sine wave of each channel. Enveloping the signal also eliminates the negative part of the signal, but the resulting signal is not still easily detectable by a device. Since the signal passed through the steel mold includes noises with higher frequencies the signal can be wavy for each channel after enveloping. A low pass filter is designed and employed for each channel to eliminate these noises with higher frequencies.

Figure 15B:
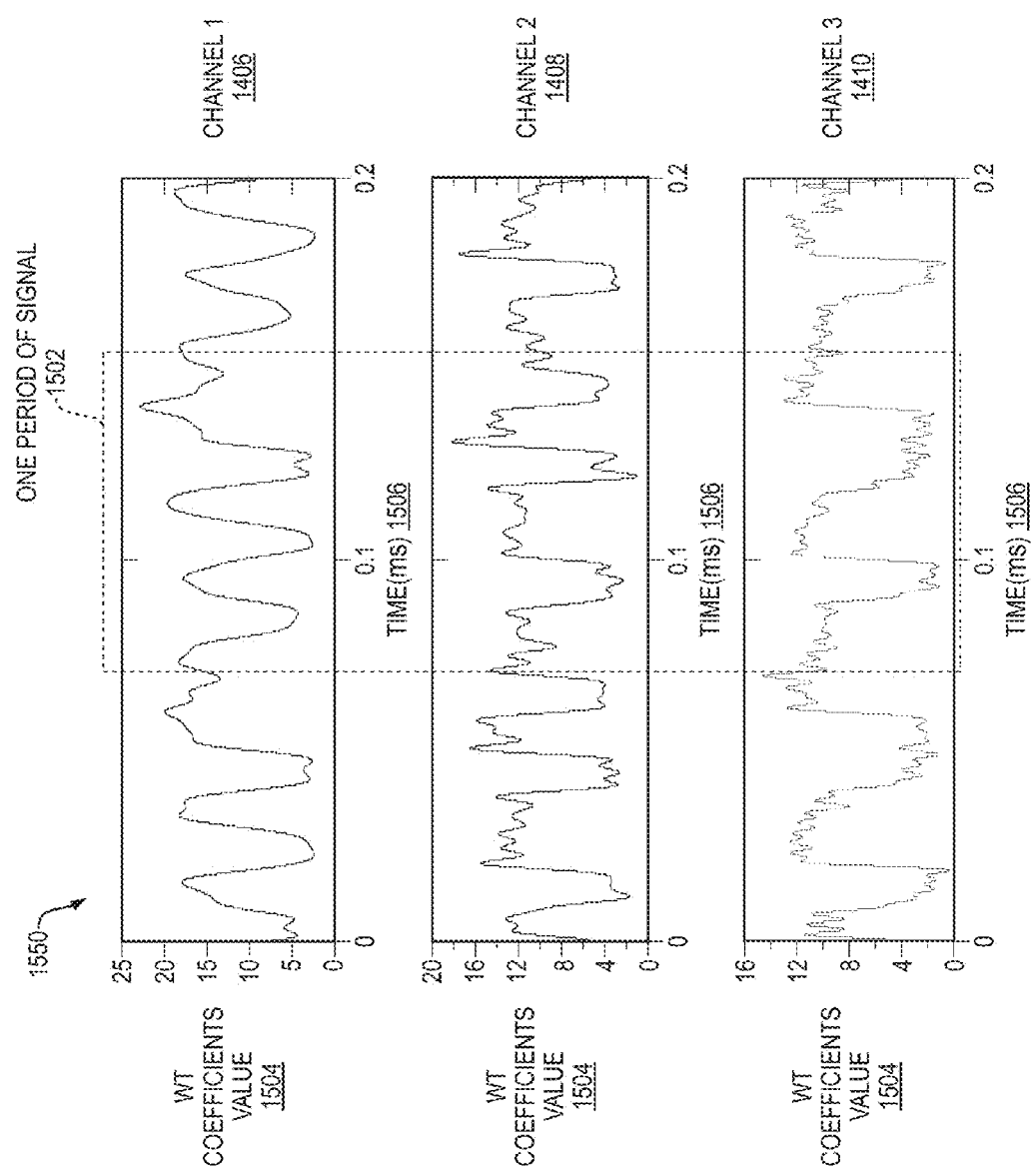
FIG. 15B is a diagram illustrating a reconstructed signal after enveloping and low pass filtering.

FIG. 15B is a diagram 1550 illustrating a reconstructed signal after enveloping and low pass filtering. Each channel 1406, 1408, 1410 shows the signal without the underlying carrier signal due to the enveloping and low pass filtering.

FIG. 15C is a diagram 1570 illustrating an example embodiment of thresholding to differentiate the individual "0" and "1" bits to extract the digital data from the filtered signals of FIG. 15B. If the thresholding value is set to be low, any noise effecting the signal with higher amplitude than the thresholding cutoff value when a "0" digit is being transmitted could result in a wrong calculation. Further, a "1" digit is reported instead, which results in higher error values for each channel bits. On the other hand, if the thresholding cutoff value is too high, then the results could be again misreported for a "1" digit as a "0" value when the digit "1" is in fact getting transmitted. Therefore, a proper cutoff value has been selected using the half value of the signal amplitude range to avoid having misreported digits and getting the minimum error values for the received signal bits. The same signal transmission and demodulation process has been done for the other tests and results showed that the proposed acoustic wireless sensor can be used to transmit the data from the mold cavity to the outside of the mold which is shielded.

The effect of SNR on the output signal has been investigated by calculating the average power when the digit "1" and "0" are present in all 8-digit combinations. The received signal is simulated under different transmission rates, as listed in Table 1. When the transmission rate is lower than 10 kB/s, the SNR of output is consistently higher than 6.4 dB, indicating that the amplitude of the signal (related to the melt pressure, temperature and velocity) in transmitting the digit "1" is approximately four times the amplitude of the noise when transmitting the digit "0". Such a SNR is sufficient for extracting data reliably using thresholding method.

TABLE 1

Comparison of SNR at different transmission rates

| | | Max Tr. Rate | | | | |
|---|---|---|---|---|---|---|
| | | 2 kB | 4 kB | 8 kB | 10 kB | 12 kB |
| SNR of | CH #1 | 12.6 | 12.5 | 10.3 | 6.4 | 5.3 |
| Output | CH #2 | 16.2 | 15.1 | 13.2 | 7.6 | 7.0 |
| [dB] | CH #3 | 15.4 | 14.2 | 12.7 | 7.4 | 6.9 |

Figure 16:
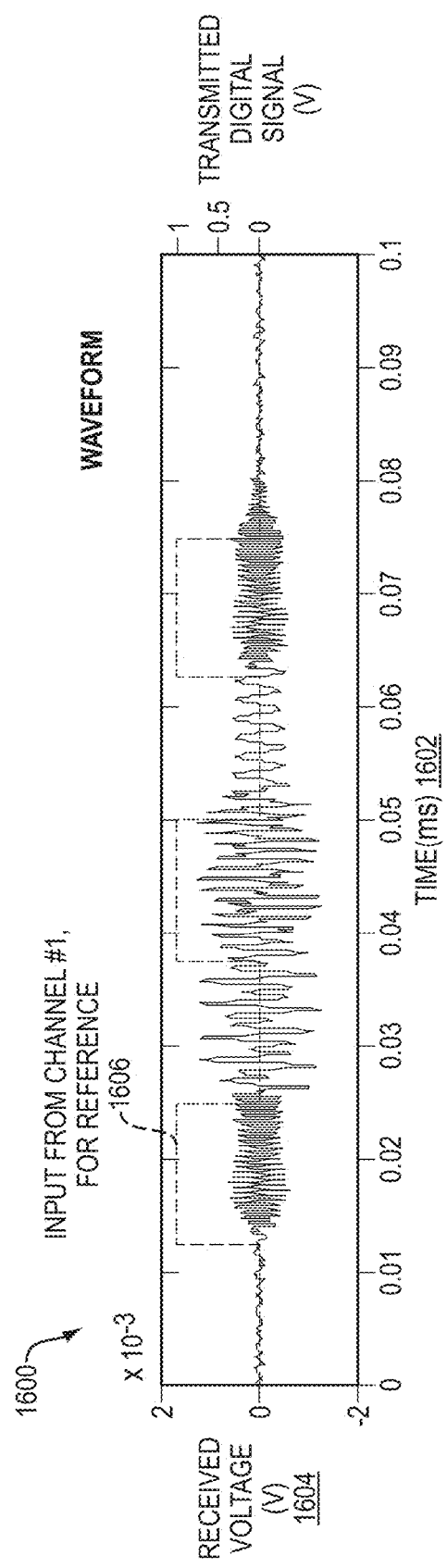
FIG. 16 is a chart diagram illustrating a typical cycle of a recorded waveform of a first four digits (Digit 1-4) of a set of 8-digit data streams.

FIG. 16 is a chart diagram 1600 illustrating a typical cycle of the recorded waveform of the first four digits (Digit 1-4) of a set of 8-digit data streams. In each of the transmitted data sets, the pressure, temperature, and velocity values (in Volts) are represented by an 8-bit digital word (corresponding to a resolution of 1/128=0.0078) transmitted through channel 1, 2, and 3, respectively.

Figure 17:
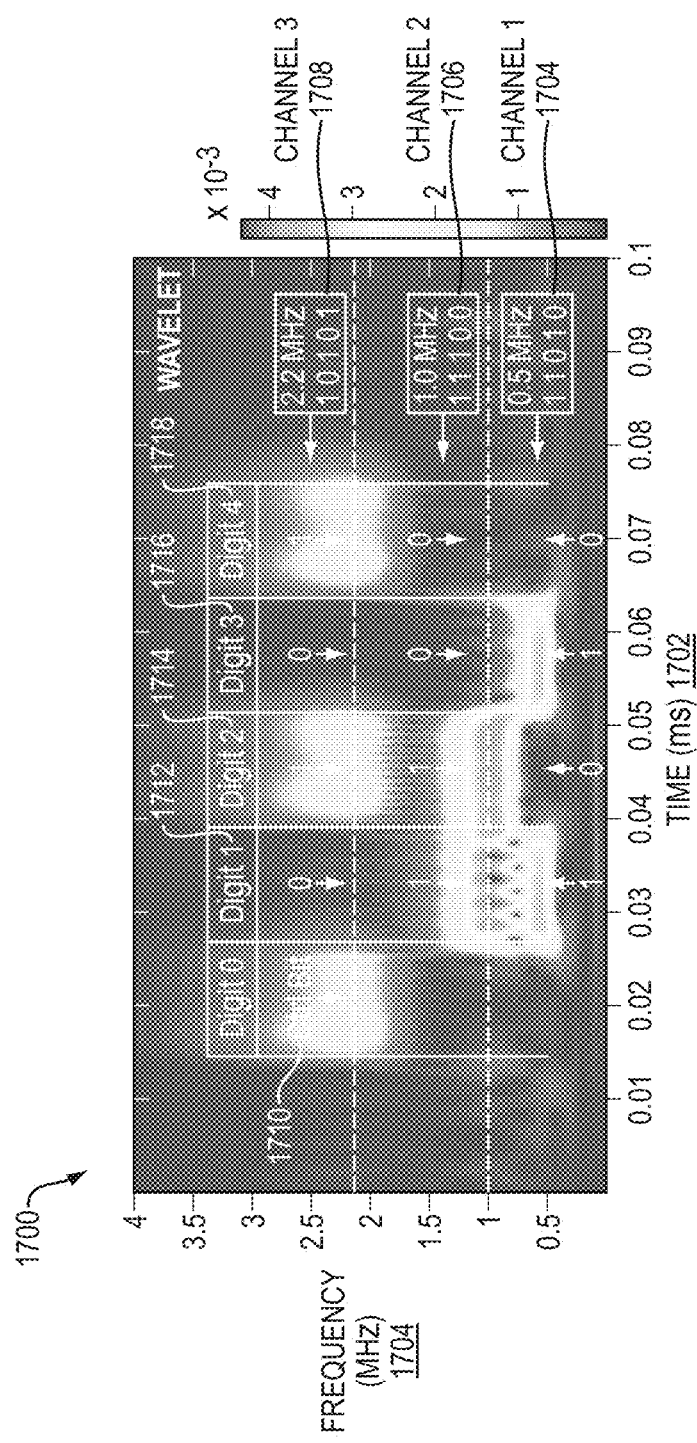
FIG. 17 is a chart diagram illustrating a typical wavelet of an acoustic transmission.

FIG. 17 is a chart diagram 1700 illustrating a typical wavelet of the acoustic transmission. The beginning of each data set transmitted is marked by an additional control bit (Digit 0) 1710. In FIG. 16, the control bit is shown as "input from channel #1 1606." Referring to FIG. 17, since the three parameters are transmitted simultaneously, Digit 0 for Channel 2 1706 and Channel 3 1708 are not applied, to save transmission energy. In another embodiment, a fourth channel (not shown) using a fourth carrier frequency can transmit a control bit. The coded data modulate the three carriers and subsequently added together as input to the transmitter model. The time length for each digit is set to 12.5 µs, which corresponds to a maximum data transmission rate of 8 kB/s. Such a bit rate, if applied to monitoring injection molding, enables the sensor to report the melt states every 0.125 ms, which is an order of magnitude higher than dynamic features such as overshoots (duration >1 ms) in the melt pressure and temperature.

Figure 18:
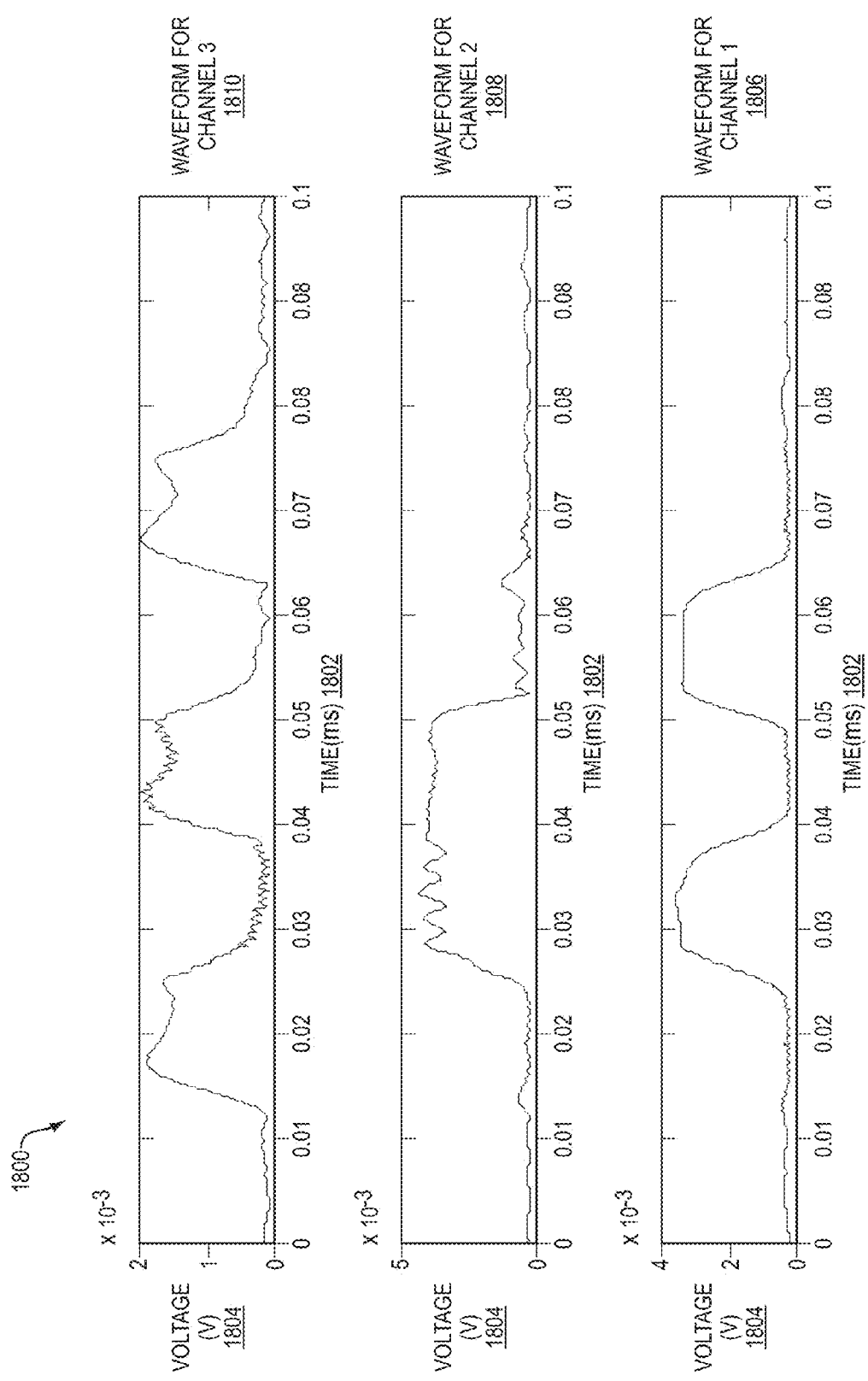
FIG. 18 is a chart diagram illustrating extracted parameters from a wavelet transform.

FIG. 18 is a chart diagram 1800 illustrating extracted parameters from a wavelet transform. The waveforms for the three channels 1806, 1808, 1810 are successfully separated, and the transmitted data bits are properly identified. The effect of signal-to-noise ratio (SNR) on the output signal has been investigated at different data transmission rates, from 2 kB/s to 16 kB/s. Amplitude of the noise is measured as 0.8 mV in cases when the mold is open, i.e. where there is no data transmitted from the sensor. The amplitude of signal is calculated by taking the average amplitude when "1" and "0" are present in all the data during an injection molding cycle. The SNR is then calculated as:

$$SNR = 20 * \log(A_{Signal}/A_{Noise})$$

Figure 19:
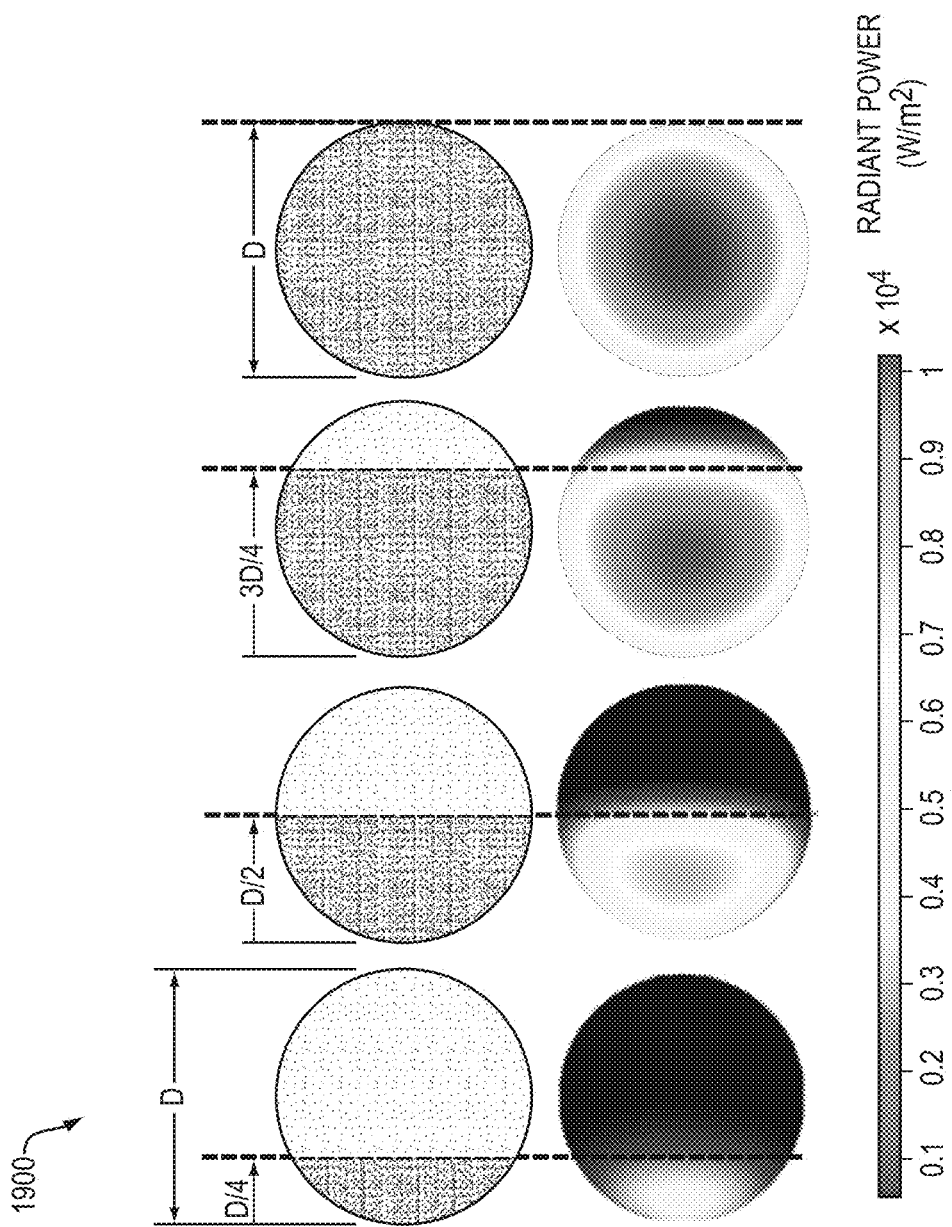
FIG. 19 is a diagram illustrating distribution of radiant flux density on a surface of the infrared detector when a plastic melt front reaches ¼, ½, ¾, and a complete diameter of the infrared detector window, under a melt front velocity of 260 mm/s.

FIG. 19 is a diagram 1900 illustrating distribution of radiant flux density on the surface of the IR detector when the plastic melt front reaches ¼, ½, ¾, and the complete diameter of the IR detector window, under a melt front velocity of 260 mm/s. As an example, when the melt covers ¼ diameter of the IR detector window, the radiating power concentrates on the center of the covered area with a density of 2,480 W/m². In comparison, the power concentration is lower at the melt front (1,800 W/m²) where the source of IR radiation is discontinued. The IR will also be diffused in the uncovered portion on the IR detector where a minimum power of 800 W/m² was calculated from the simulation model. When the melt completely covers the IR detector, the power concentration will be located at the center of the IR detector.

By integrating the heat flux on the sensing surface of the IR detector, the total power absorbed by the IR detector can be determined. The corresponding voltage output of the IR detector was then simulated in the numerical model. To confirm the melt velocity measurement method, the simulation was repeated by setting the melt front velocities at 260 mm/s, 330 mm/s, and 400 mm/s, respectively [10].

Figure 20:
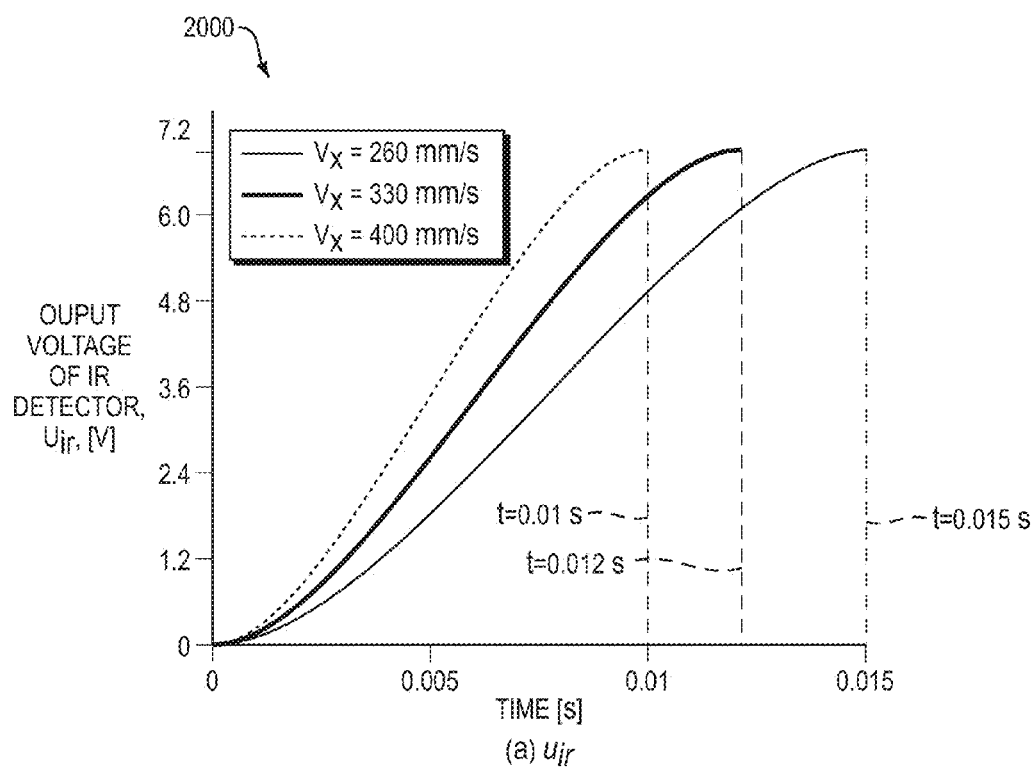
FIG. 20 is a diagram illustrating output voltage of an infrared detector over time.

FIG. 20 is a diagram 2000 illustrating output voltage of the IR detector over time. As the melt front starts to cover the IR detector at t=0, the sensor output voltage begins increasing from zero. The effect of the set melt velocity on the measured velocity can be neglected because the IR wave propagates at the speed of light. Thus, all the curves obtained show a similar and consistent trend of time-dependent variation. According to the voltage response value of the IR detector (300 [V/W]), the voltage output reaches the maximum voltage of 6.9 V, when the IR detector is fully covered by the melt.

Figure 21:
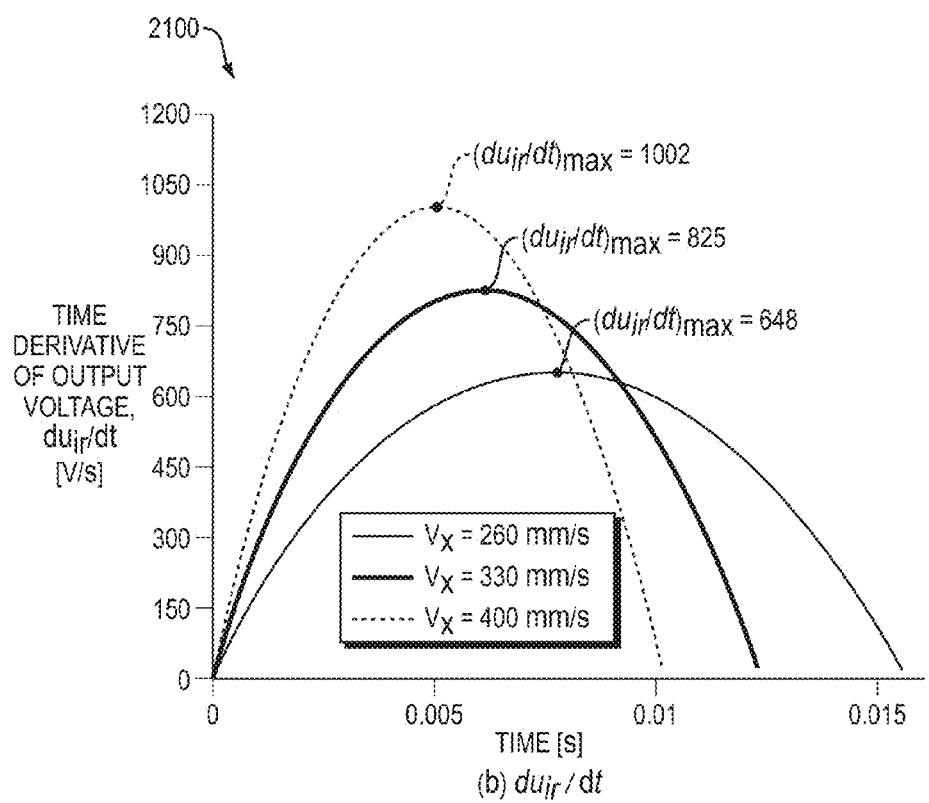
FIG. 21 is a diagram illustrating time derivative of an output voltage of an infrared detector.

FIG. 21 is a diagram 2100 illustrating time derivative of the output voltage of the IR detector. Based on Eq. (5), the time derivative of the output voltage can be calculated for each of the three simulations, as shown in FIG. 7B. The changing rate of the output voltage reaches the maximum value when the melt front approximately reaches the center of the IR sensor. By substituting the values of $(du_{ir}/dt)_{max}$ into Eq. (6), the velocity values was calculated, as listed in Table II. The error between calculated and set velocity can be less than 0.12%. Furthermore, the results indicate that the effect of IR diffusion on the velocity measurement is not significant, due to the fact that the majority of the radiated power concentrates on the portion being covered by the plastic melt.

TABLE II

SET AND CALCULATED VELOCITY

| Simulation | Set Velocity [mm/s] | $(du_{ir}/dt)_{max}$ [V/s] | Calculated $v_x$ [mm/s] | Error [%] |
|---|---|---|---|---|
| 1 | 260 | 648 | 259.7 | −0.08 |
| 2 | 330 | 825 | 329.5 | −0.12 |
| 3 | 400 | 1002 | 400.2 | 0.05 |

The melt temperature may vary from 200° C. to 400° C., given that the initial conditions required for processing various plastic materials are different. The melt temperature determines the radiated power as well as the output of the IR detector according to its fourth power, based on the Stephan-Boltzmann law as shown in Eq. (1) and Eq. (3). The simulation can be repeated by setting the melt temperature at 210° C., 260° C., 310° C., and 360° C., respectively to evaluate the effect of melt temperature in relation to the new velocity sensing method. Also, the diameter of the IR detector was varied from 4 mm to 6 mm.

Figure 22:
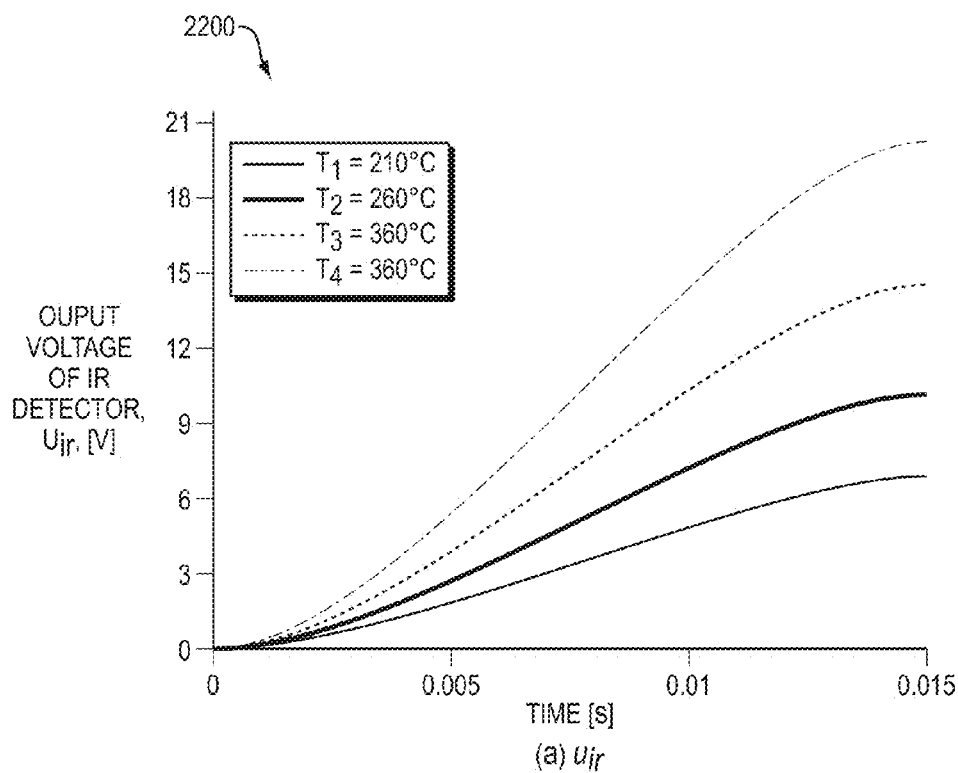
FIGS. 22-23 are diagrams and illustrating the output voltage and its time derivative simulated with a set velocity of 260 mm/s and infrared diameter being 4 mm.
Figure 23:
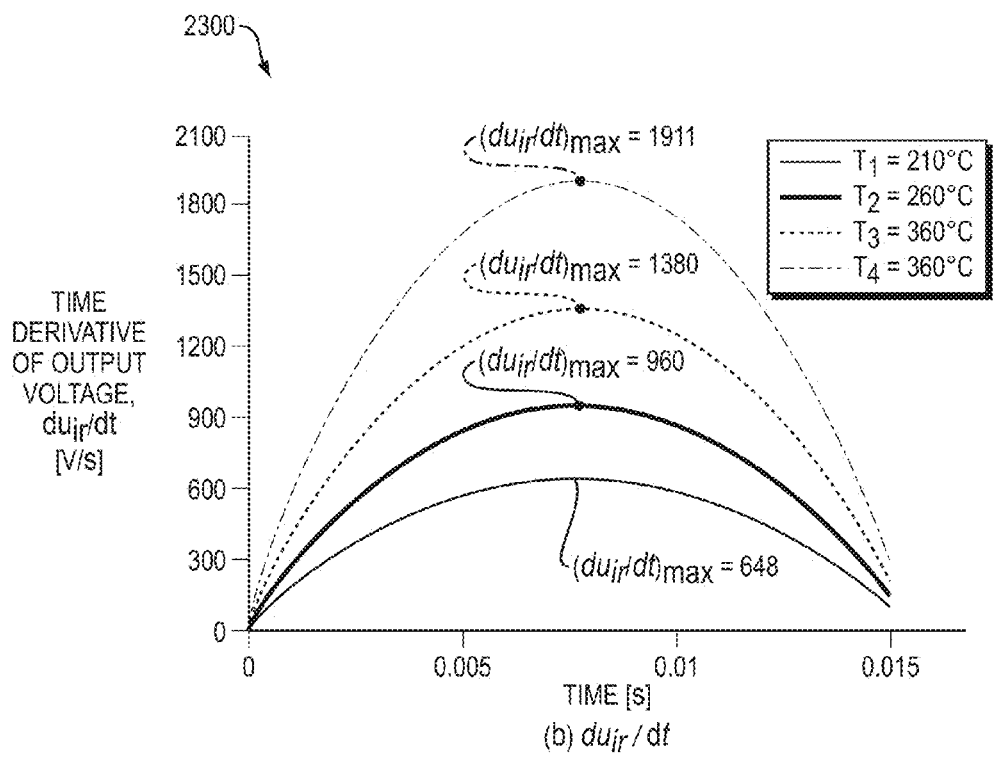

FIGS. 22-23 are diagrams 2200 and 2300 illustrating the output voltage and its time derivative simulated with a set velocity of 260 mm/s and IR diameter being 4 mm. The average error between the measured and set velocities is consequently listed in Table III.

TABLE III

CALCULATED ERROR FOR DIFFERENT MELT SENSOR AND IR DETECTOR DIAMETER

| D | Melt Temperature | | | |
|---|---|---|---|---|
| (mm) | 210° C. | 260° C. | 310° C. | 360° C. |
| 4 | +0.20% | −0.12% | −0.25% | −0.26% |
| 5 | +0.05% | −0.16% | −0.06% | −0.10% |
| 6 | −0.04% | +0.05% | +0.04% | −0.06% |

Error value can change randomly when the melt temperature or IR detector diameter increase/decreases. A major factor leading to the error is the time step length (sampling period) set for the transient analysis because the simulation did not consider disturbance factors. The maximum value of $du_{ir}/dt$ is determined by the time step when the melt front is closest to the center of the IR detector. The overall maximum error is less than 0.25%, which indicates a high accuracy of the new velocity measurement method.

Figure 24:
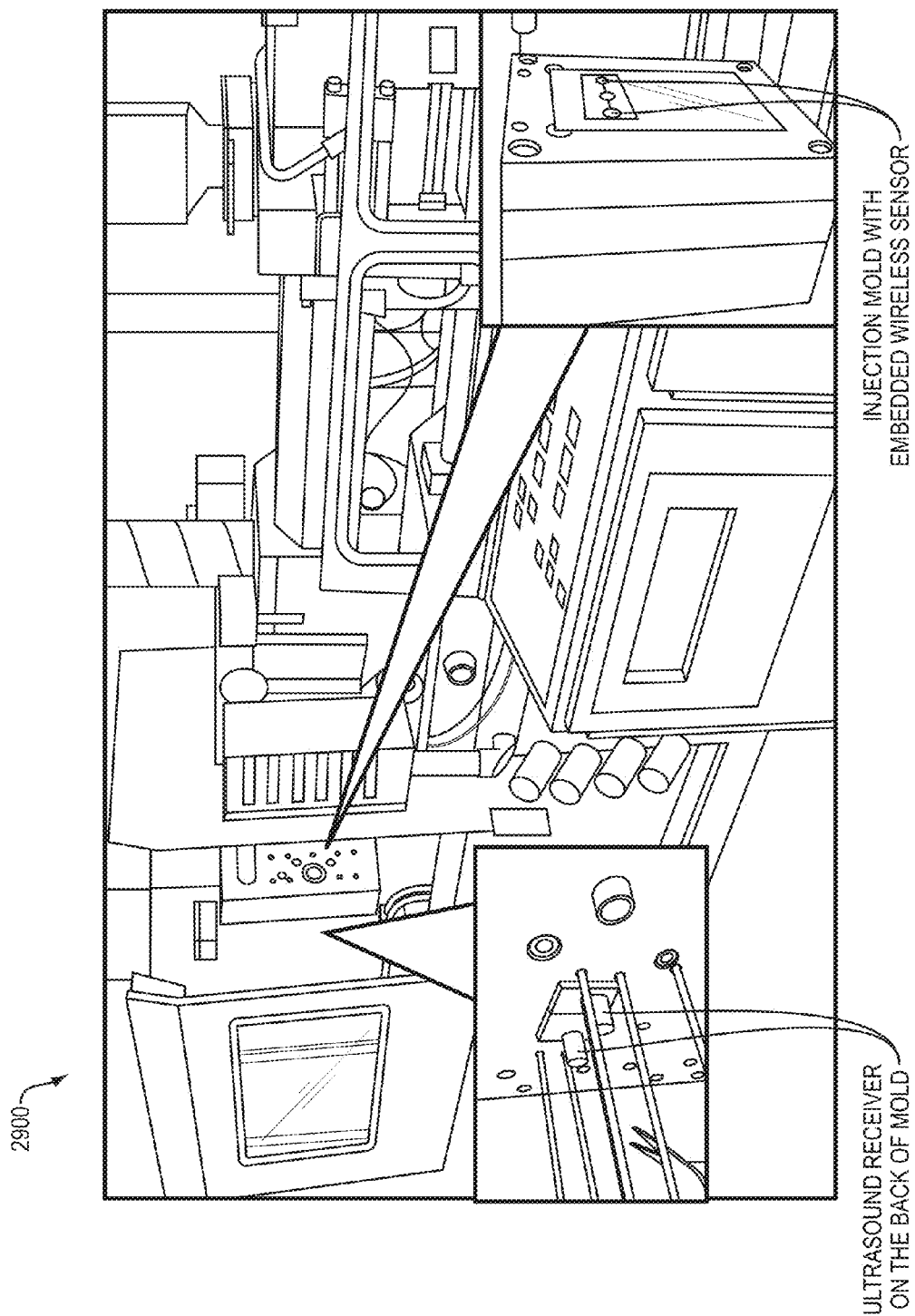
FIG. 24 is a block diagram illustrating an example embodiment of an injection molding machine.

FIG. 24 is a block diagram 2400 illustrating an example embodiment of an injection molding machine. Based on the simulation results, the multivariate sensor can be prototyped and tested in three customized molds (e.g., where thickness=40, 80, 120 mm) of a MILACRON injection molding machine. The acoustic wave can be sampled by an ultrasound receiver installed at the back of the mold. Distance between the transmitter and receiver can be 40 mm in one embodiment. The signal waveforms are sampled and recorded by a software interface, for example, developed using the LabVIEW platform.

A 40 mm-thick aluminum mold can be employed for sensor performance evaluation. A 5 mm-diameter SFH229 IR detector can be embedded in the stationary part of the injection mold. The injection molding machine can be run under two different screw speeds set for the injection molding machine: 60 mm/s and 80 mm/s, respectively. The set speeds can determine the speed of the melt forced through the barrel into the mold cavity. The melt front velocity in the two cases can be estimated as 260 mm/s and 400 mm/s, respectively, by using molding process simulation program developed in [12]. Since the melt front velocity is not directly accessible by other sensors, the simulated values can be used as reference to evaluate the developed sensing method. The signal from the IR detector can be processed and sampled by a NI-5112 data acquisition card, at a sampling rate of 5,000 Samples/second. Such a sampling rate enables acquisition of at least 60 temperature data during the period when the melt front flows across the lens at the estimated melt front velocity of 260~400 mm/s.

The multivariate sensor can be tested by using an ASTM mold with 40 mm of thickness, which is used in an all-electric 50 ton Ferromatic Milacron molding machine. The multivariate sensor is embedded in the mold, which converts the melt pressure to voltage using the piezoelectric transducers placed in the sensor structure.

The pressure sensor consists of piezoelectric stack is coupled with the mold cavity and works as the energy converter. The multivariate sensor can be tested under a range of screw speeds, from 60 to 100 mm/s, and different barrel temperatures, from 210 to 250 degrees Celsius.

TABLE IV

COMPARISON BETWEEN CALCULATED
VELOCITY AND ESTIMATED VELOCITY

| Exp. | Screw Velocity [mm/s] | Simulated Velocity [mm/s] | (dT/dt)$_{max}$ [T/s] | Calculated v$_x$ [mm/s] |
|---|---|---|---|---|
| 1 | 60 | v$_{sx1}$ = 260 | 1500 | v$_{x2}$ = 279.9 |
| 2 | 80 | v$_{sx2}$ = 400 | 2000 | v$_{x2}$ = 373.3 |
|  | 60/80 = 0.750 | v$_{sx1}$/v$_{sx2}$ = 0.650 |  | v$_{x1}$/v$_{x2}$ = 0.749 |

FIGS. 25A-B are block diagrams 2500, 2550 illustrating measured voltage from the IR detector. At the initial stage of the temperature curves (e.g. approximately from 0.1 to 0.15 second for v$_{sx}$=260 mm/s), the temperature values slightly increase as the mold is being warmed up, before the melt front reaches the IR sensor lens. When the melt front has fully covered the lens, the values of u$_{irf}$ are measured as 6.9 V for both of the two cases. The corresponding values of (du$_{ir}$/dt)$_{max}$ can be 700 V/s and 930 V/s, respectively. Based on Eq. (7), the velocity of the melt front can be calculated as v$_{x1}$=279.0 mm/s and v$_{x2}$=373.3 mm/s, as listed in Table IV. By calculating the ratio of the melt velocity using the two methods, the results from the experimental data (v$_{x1}$/v$_{x2}$=0.749) matches better with the ratio of velocity set for the screw (60/80=0.750) than using the data from the simulation model (vs$_{x1}$/v$_{sx2}$=0.650). The developed new velocity sensing method provides an accurate representation of the trend of melt front velocity variations.

Figure 26A:
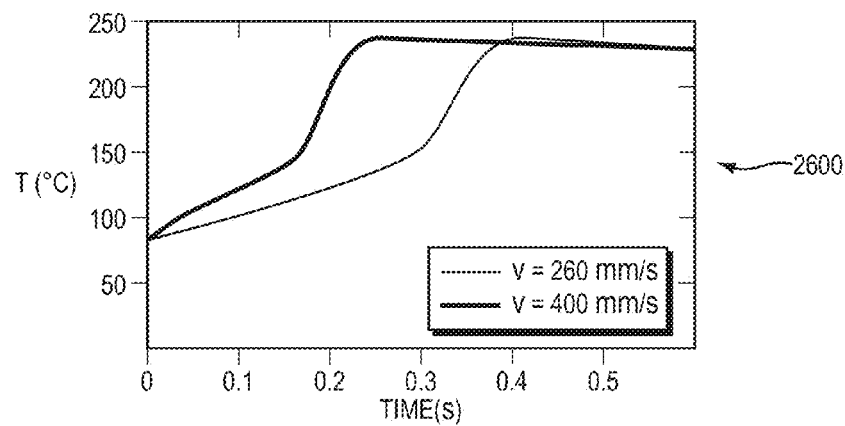
FIGS. 26A-B is a chart diagrams illustrating example temperature profiles acquired by an infrared detector and its associated ramping rate.
Figure 26B:
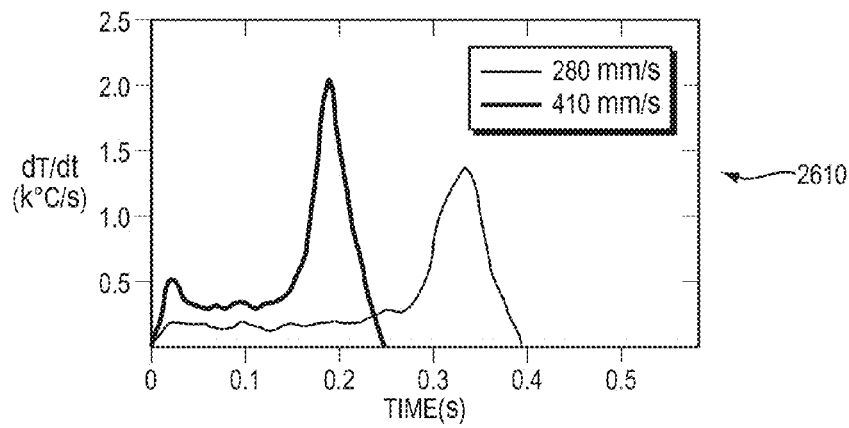

FIGS. 26A-B is a chart diagrams 2600, 2610 illustrating example temperature profiles acquired by the IR detector and its associated ramping rate. In one embodiment, the multivariate sensing method can be evaluated on a MILACRON injection molding machine. The example temperature curves can be sampled under two preset melt velocities: 260 mm/s and 400 mm/s. From the maximum values of temperature curves, the melt velocities of the two experiments can be 280 mm/s and 410 mm/s, respectively. The error of the simulation is within 7.7% of the pre-set values of the molding machine.

Uncertainty of the velocity measurement is attributed to the uncertainty in measurement of melt temperature T$_0$ and determination of the maximum rate of temperature variation (dT/dt)$_{max}$. Both of them are affected by noise associated with the injection molding process. Such uncertainties can be reduced by means of sensor calibration and filtering techniques. Based on the preliminary experiments, the total error of velocity measurement based on the temperature measurement can be less than 8%.

Figure 26C:
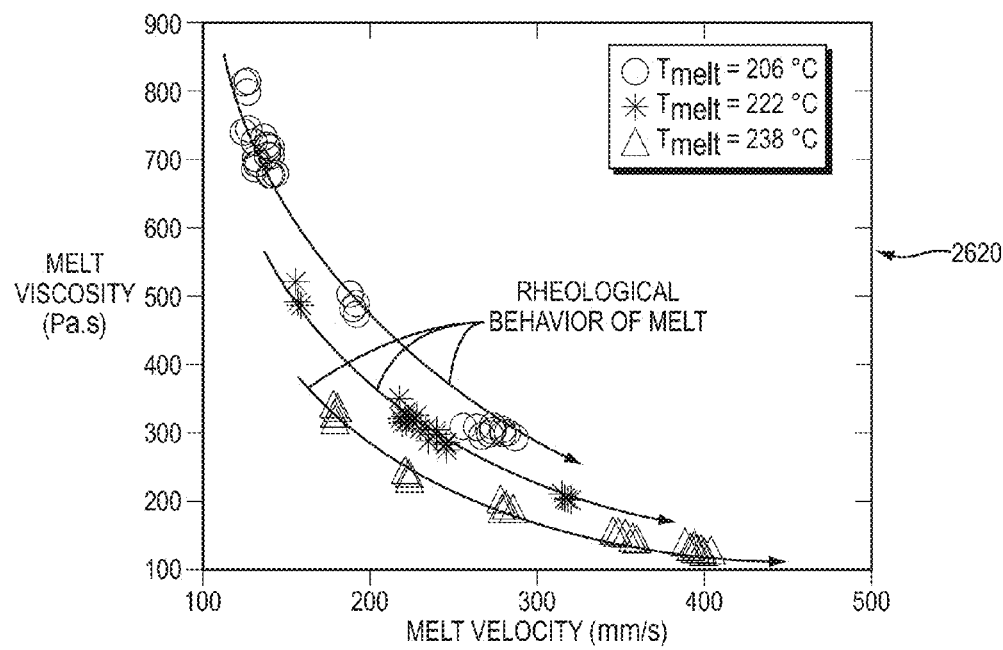
FIG. 26C is a chart diagram illustrating the melt viscosities under different temperature conditions calculated from velocity and pressure measurements.

FIG. 26C is a chart diagram 2620 illustrating the melt viscosities under different temperature conditions calculated from the velocity and pressure measurements. The melt viscosities illustrated in FIG. 3 exemplify data patterns that match rheological behavior of the polymer, including: 1) shear thinning, which causes a reduction in the viscosity when melt velocities increase, and 2) non-isothermal behavior, which decreases in the melt viscosity when melt temperatures increase.

Figure 26D:
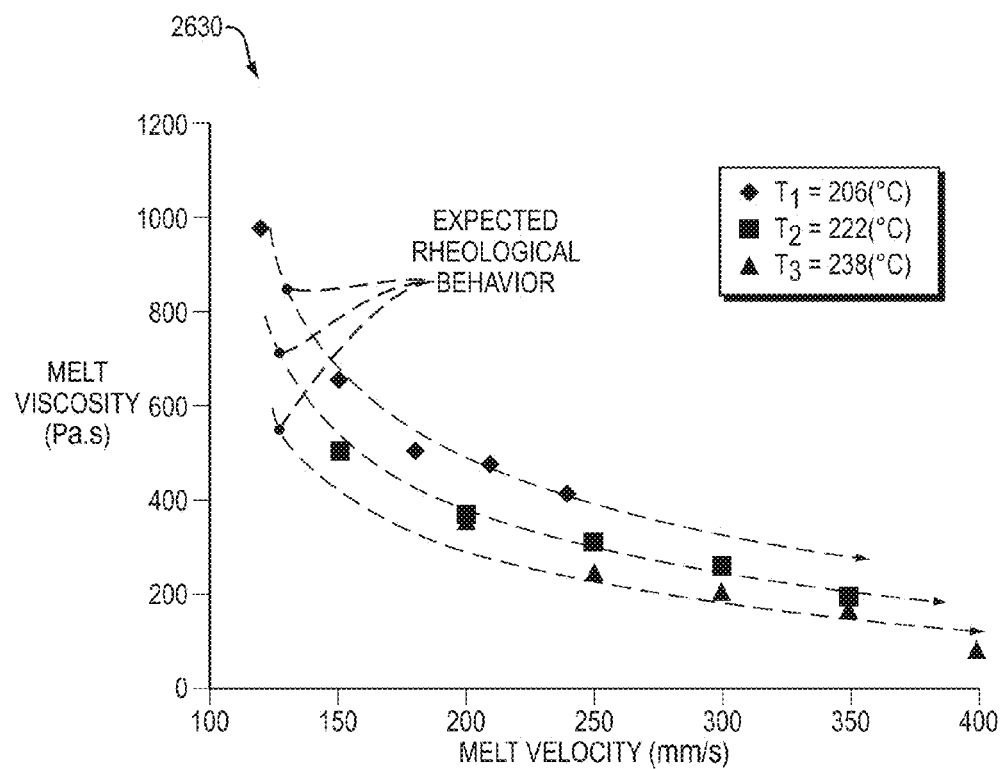
FIG. 26D is a chart diagram illustrating calculated viscosity results versus melt velocity for three dominant temperature values.

FIG. 26D is a chart diagram 2630 illustrating calculated viscosity results versus the melt velocity for the three dominant temperature values. According to the rheological behavior of the melt, as the melt temperature decreases, the melt has higher resistance to the fluid flow, and in higher melt velocities the melt shows a lower flow resistance. Therefore, FIG. 25D illustrates the expected rheological behavior of the polymer melt.

Figure 26E:
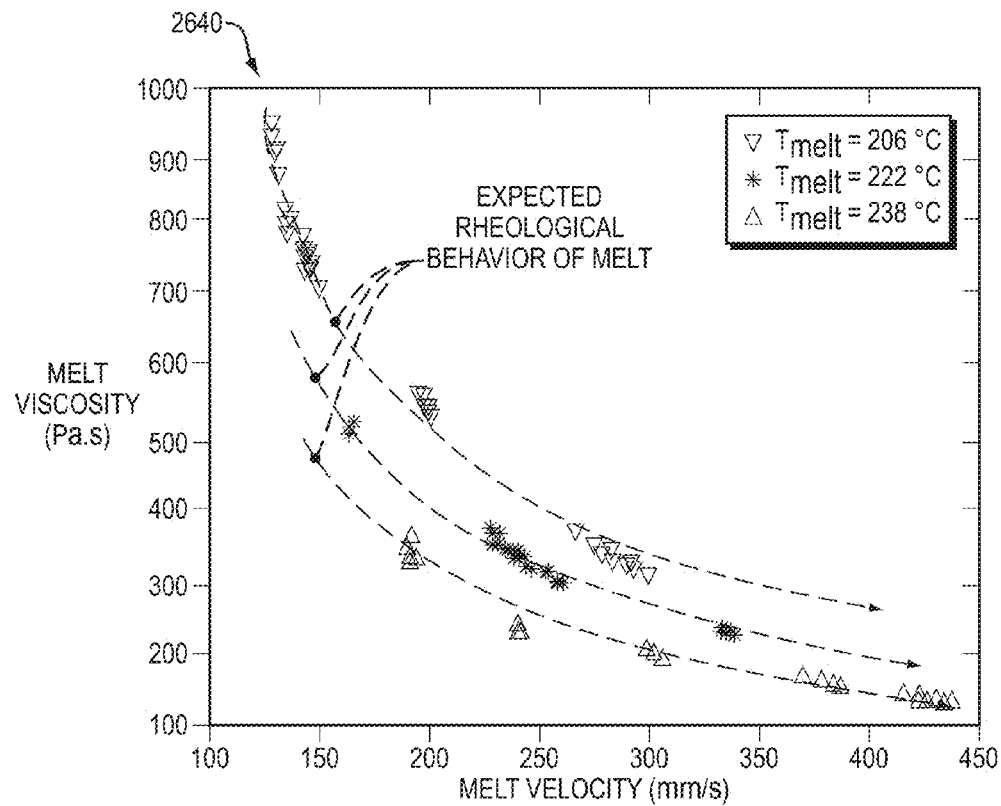
FIG. 26E is a chart diagram illustrating an example embodiment of melt viscosities for a range of melt velocities and melt temperatures.

FIG. 26E is a chart diagram 2640 illustrating an example embodiment of melt viscosities for a range of melt velocities and melt temperatures. The inferred melt viscosity values are affected by errors associated with the velocity measurement. Therefore, the multivariate sensor described herein can accurately capture the expected rheological behavior of the melt including the shear thinning and non-isothermal behavior of the melt viscosity.

Figure 27:
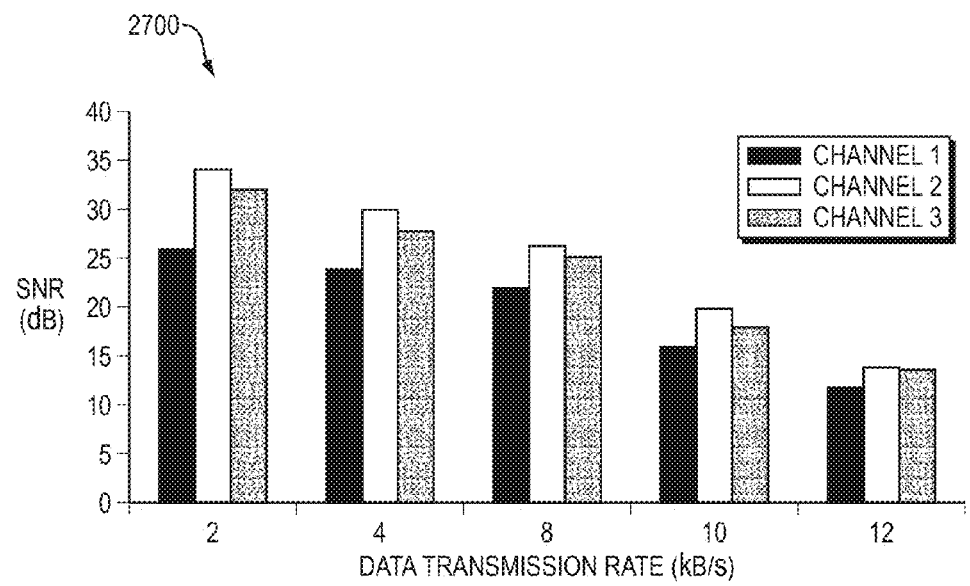
FIG. 27 is a chart diagram illustrating the measured SNR for each transmission channels.

FIG. 27 is a chart diagram 2700 illustrating the measured SNR for each of the transmission channels. When the transmission rate is below 8 kB/s, the SNR of output is consistently higher than 20 dB, indicating that the amplitude of the signal (related to the melt pressure, temperature and velocity) in transmitting the digit "1" is approximately 10 times the amplitude of the noise when transmitting the digit "0". Such a SNR is sufficient for extracting data reliably using a thresholding method. To evaluate the reliability of data transmission, three sets of 16 kB-long data can be simultaneously transmitted through three channels at 8 kB/s. The test was repeated on three customized molds of 40, 80, and 120 mm thickness. For each mold, the Bit Error Rate (BER) of the received data at different threshold values (normalized by the peak value of the extracted data in each channel) can be calculated.

Figure 28:
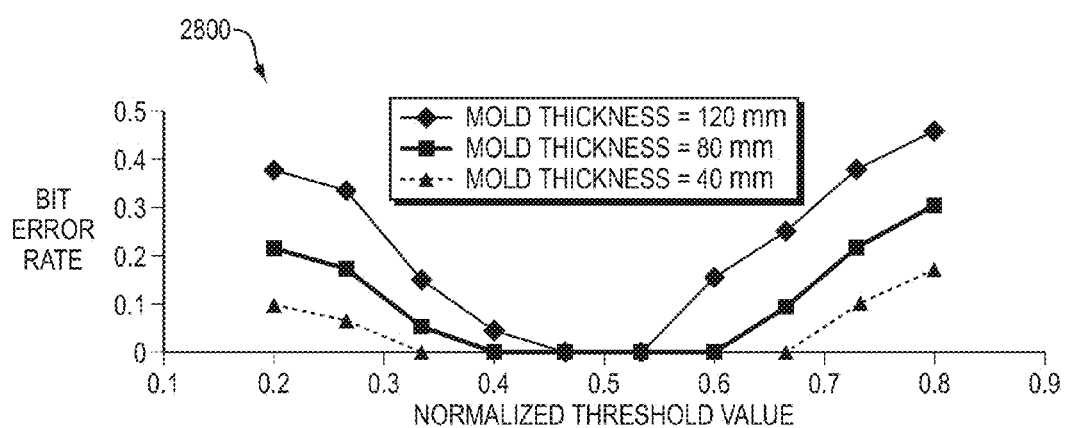
FIG. 28 is a chart diagram illustrating the BER of a received signal for different transmission distances at a threshold value of 0.5.

FIG. 28 is a chart diagram 2800 illustrating the BER of a received signal for different transmission distances at a threshold value of 0.5. A zero BER indicates that all the transmitted data can be received and identified correctly.

There are three phases in an injection molding process: filling, packing, and cooling. Melted polymer flows into the mold to fill the cavity in the first phase (filling). In the second phase (packing) more melted polymer is injected to prevent part shrinkage due to the cooling. The third phase (cooling) starts with the first phase and ends up when the polymer is solidified more than 80 percent. Melt velocity is an important parameter which has to be monitored and controlled in the filling phase because the effect of the shear stress and shear strain on the part. Providing a constant melt flow increases the harmony of the material molecular orientation and thus results in less internal stress.

Many methods can measure the viscosity of a fluid. A capillary method defines viscosity based on the time for a specific amount of fluid to flow through a tube under a specific pressure, in the oscillating vessel method a specific force is applied to fluid in a vessel and fluid motion is damped due to the energy dissipation. Viscosity is accordingly measured based on the related time period for fluid motion decrement. A rotating cylinder method measures the fluid viscosity based on the induced torque to a cylinder where there is another coaxial rotating cylinder with a constant speed inside and fluid is filled between these cylinders. In an injection molding process, melt viscosity is in direct relation with pressure variation. Higher viscosity of the melt generally requires higher pressure to enable proper injection in the cavity. On the other hand, lower viscosity results in quality problems, such as flashing. In traditional methods, pressure can be used as an estimated indicator for viscosity because of the difficulties in measuring viscosity of the melt directly. The melt shear stress is in direct relation with the nozzle pressure, and the shear rate is in direct relation with the flow rate. Therefore, viscosity is determined as the ratio of nozzle pressure to injection rate, and if the flow rate is assumed to be constant, the only variable is the nozzle pressure. An online viscosity measuring method based on pressure drop and fluid flow rate for a fully developed fluid is investigated, where two pressure sensors are required to monitor the pressure.

Figure 29:
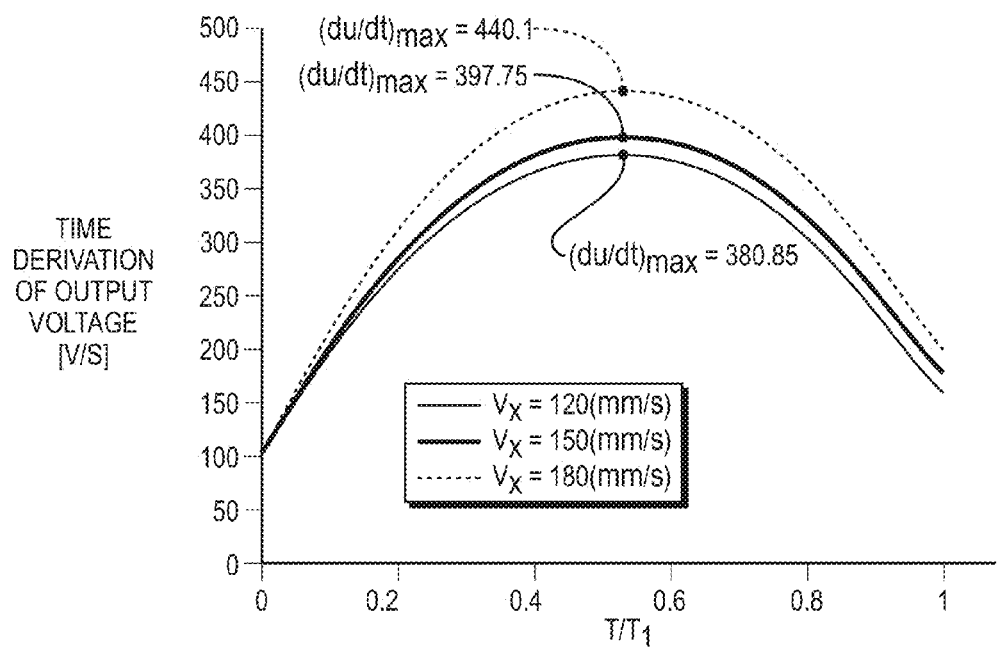
FIG. 29 is a chart diagram illustrating an example embodiment of a time derivative of the measured output voltage.

FIG. 29 is a chart diagram 2900 illustrating an example embodiment of a time derivative of the measured output voltage.

Figure 30:
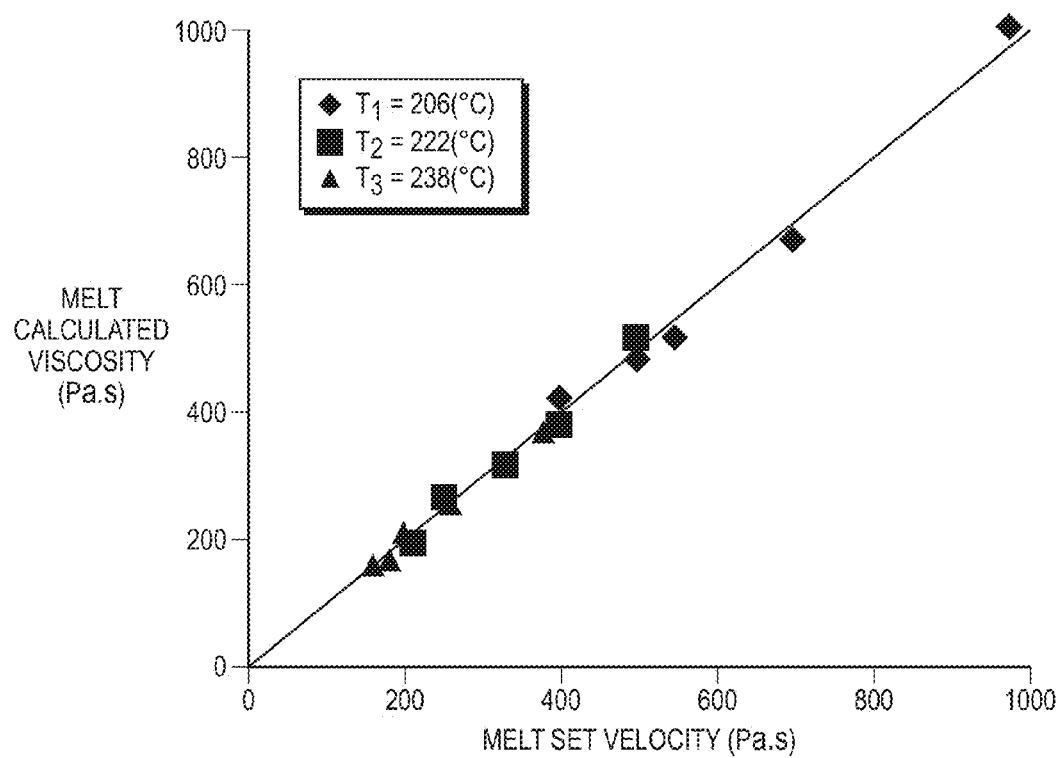
FIG. 30 is a chart diagram illustrating an example embodiment of a calculated melt viscosity based on melt set viscosity for different temperatures.

FIG. 30 is a chart diagram 3000 illustrating an example embodiment of a calculated melt viscosity based on melt set viscosity for different temperatures. FIG. 7 demonstrates the effect of melt velocity and temperature based on the common situations for the polymer injection molding for three different temperatures of $T_1=206$, $T_2=222$, and $T_3=238$ degrees of Celsius. The range of the melt velocities corresponding to each temperature have been set in the range of 120 to 240, 150 to 250, and 200 to 400 millimeter per second for the numerical analysis. The viscosity values are calculated and compared with the set viscosities in the simulation and results.

The comparison of the set and calculated viscosities depict a good correlation, the related error values for inferred melt viscosities based on melt velocity and temperature is also presented in Table. 1. However, the error of the calculated viscosity is due to the two following reasons. First, the viscosity equation is derived based on a two dimensional space assumption for the fluid flow, and second, the fluid velocity is assumed to be just a function of z which means $v=w=0$. However, a simulated numerical model in a three dimensional space considers all the parameters.

TABLE 1

CALCULATED ERROR FOR DIFFERENT MELT VELOCITY AND TEMPERAUTRE

| $T_1$ [° C.] | Velocity [mm/s] | 240 | 210 | 180 | 150 | 120 |
|---|---|---|---|---|---|---|
| | Set μ [Pa · s] | 400 | 500 | 550 | 700 | 980 |
| | Error [%] | 5.65 | −3.12 | −6.42 | −4.31 | 2.24 |
| $T_2$ [° C.] | Velocity [mm/s] | 350 | 300 | 250 | 200 | 150 |
| | Set μ [Pa · s] | 210 | 250 | 330 | 400 | 500 |
| | Error [%] | −6.48 | 6.37 | −4.04 | −4.88 | 3.17 |
| $T_3$ [C.] | Velocity [mm/s] | 400 | 350 | 300 | 250 | 200 |
| | Set μ [Pa · s] | 160 | 180 | 200 | 260 | 380 |
| | Error [%] | 0.53 | −5.95 | 6.47 | −1.72 | −3.46 |

The sampling period of the simulated voltage data effects on the maximum value of the detected voltage ramp rate because the output voltage of the piezoelectric sensor in the numerical analysis is simulated using a time dependent study model. In fact, the maximum value of the time derivation of voltage is determined when the melt crosses the centerline of the sensor.

Embodiments or aspects of the present invention may be implemented in the form of hardware, software, or firmware. If implemented in software, the software may be any form of software capable of performing operations consistent with the example embodiments disclosed herein. The software may be stored in any non-transient computer readable medium, such as RAM, ROM, magnetic disk, or optical disk. When loaded and executed by processor(s), the processor(s) are configured to perform operations consistent with the example embodiments disclosed herein. The processor(s) may be any form of processor(s) capable of being configured to execute operations as disclosed herein. In an example embodiment, the processor(s) may execute instruction(s) of the software that calculate melt viscosity from inputs of pressure, temperature, and/or melt velocity.

What is claimed is:

1. A sensor, comprising:
    an infra-red thermal detector;
    a pressure sensor configured to produce charge as a function of pressure, the charge being available as power to a circuit;
    a processor configured to convert output from the thermal detector and the pressure sensor and to output coded representations of pressure, temperature, and melt velocity; and
    an acoustic transmitter configured to transmit the coded representations via an acoustic medium, the processor and acoustic transmitter being powered by the charge produced by the pressure sensor.

2. The sensor of claim 1, wherein the processor is further configured to output a coded melt viscosity.

3. The sensor of claim 1, wherein the pressure sensor is a piezo-electric transducer.

4. The sensor of claim 1, wherein the processor outputs the coded representations by summing products of binary representations of pressure, temperature, and melt velocity and respective carrier waves.

5. The sensor of claim 1, wherein the processor is a sensor processor and further comprising an acoustic receiver and external processor, the acoustic receiver being configured to receive the coded representations via the acoustic medium;
    and the external processor being configured to determine binary representations of pressure, temperature, and melt velocity.

6. The sensor of claim 5, wherein the acoustic receiver is further configured to calculate melt viscosity as a function of melt velocity.

7. The sensor of claim 1, further comprising an injection mold, wherein the sensor is embedded within the injection mold, and wherein the thermal detector is configured to monitor material within the injection mold.

8. The sensor of claim 1, wherein the processor converts the output from the infra-red thermal detector to the melt velocity based on a rate that a lens of the infra-red thermal detector is covered.

9. The sensor of claim 8, wherein the infra-red thermal detector is arranged to measure flow of material being measured in a direction normal to the flow of material.

10. A method of sensing a viscous compound, comprising:
    detecting infra-red thermal data of the viscous compound through use of a thermal detector;
    sensing pressure by producing a charge as a function of pressure applied to a pressure sensor by the viscous compound, the charge available as power to a circuit;
    converting output from the infra-red thermal data and from the sensed data by a processor to determine a corresponding temperature, pressure, and melt velocity of the viscous compound;
    outputting coded representations of the temperature, pressure, and melt velocity;
    transmitting the coded representations via an acoustic medium; and
    powering the detector, processor, and acoustic transmitter by the charge produced by the pressure sensor.

11. The method of claim 10, further comprising outputting a coded melt viscosity.

12. The method of claim 10, wherein sensing pressure employs a piezo-electric transducer.

13. The method of claim 10, wherein outputting the coded representations includes summing products of binary representations of temperature, pressure, and velocity and respective carrier waves.

14. The method of claim 10, further comprising:
    receiving the coded representations via the acoustic medium; and
    determining binary representations of pressure, temperature, and melt velocity.

15. The method of claim 14, further comprising calculating melt viscosity as a function of melt velocity.

16. The method of claim 10, wherein the thermal detector, pressure sensor, processor and acoustic transmitter compose a sensor, the method further comprising embedding the sensor in an injection mold in an orientation enabling the sensor to sense temperature and pressure of a viscous material within the injection mold.

17. The method of claim 10, wherein converting the output from the infra-red thermal data includes converting the output from the infra-red thermal detector to the melt velocity based on a rate that a lens of the infra-red thermal detector is covered.

18. The method of claim 17, wherein the infra-red thermal detector data is detected by an infra-red thermal detector arranged to measure flow of material being measured in a direction normal to the flow of material.

19. A sensor, comprising:
an infra-red thermal detector;
a pressure sensor configured to produce charge as a function of pressure, the charge available as power to a circuit;
a processor configured to convert output from the thermal detector and pressure sensor and output coded representations of pressure and temperature; and
an acoustic transmitter configured to transmit the coded representations simultaneously in a carrier wave via an acoustic medium, the processor and acoustic transmitter powered by the charge produced by the pressure sensor.

20. The sensor of claim 19, wherein the processor is further configured to output at least one of a coded melt velocity and a coded melt viscosity.

21. The sensor of claim 19, wherein the pressure sensor is a piezo-electric transducer.

22. The sensor of claim 19, wherein the processor outputs the coded representations by summing products of binary representations of pressure and temperature and respective carrier waves.

23. The sensor of claim 19, wherein the processor is a sensor processor and further comprising an acoustic receiver and an external processor, the acoustic receiver being configured to receive the coded representations via the acoustic medium and the external processor being configured to determine binary representations of pressure and temperature.

24. The sensor of claim 23, wherein the acoustic receiver is further configured to calculate melt velocity as a function of temperature and melt viscosity as a function of melt velocity.

25. The sensor of claim 19, wherein the thermal detector, pressure sensor, processor, and acoustic transmitter compose a sensor, and wherein the sensor is a component in an assembly further comprising an injection mold, wherein the sensor is embedded within the injection mold and configured to sense temperature and pressure of a viscous compound within the injection mold.

26. The sensor of claim 19, wherein the processor converts the output from the infra-red thermal detector to the melt velocity based on a rate that a lens of the infra-red thermal detector is covered.

27. The sensor of claim 26, wherein the infra-red thermal detector is arranged to measure flow of material being measured in a direction normal to the flow of material.

28. A method of sensing a viscous compound, comprising:
detecting infra-red thermal data of a viscous compound through use of a thermal detector;
sensing pressure by producing a charge as a function of pressure applied to a pressure sensor by the viscous compound, the charge available as power to a circuit;
converting output from the infra-red thermal data and from the sensed data by a processor to determine a corresponding temperature, pressure, and melt velocity of the viscous compound;
outputting coded representations of the temperature and pressure;
transmitting the coded representations simultaneously in a carrier wave via an acoustic medium through use of an acoustic transmitter; and
powering the detector, processor, and acoustic transmitter by the charge produced by the sensing.

29. The method of claim 28, wherein the processor is further configured to output at least one of a coded melt velocity and a coded melt viscosity.

30. The method of claim 28, further comprising sensing pressure by employing a piezo-electric transducer.

31. The method of claim 28, further comprising outputting the coded representations by summing products of binary representations of temperature and temperature and respective carrier waves.

32. The method of claim 28, further comprising:
receiving the coded representations via the acoustic medium; and
determining binary representations of pressure and temperature.

33. The method of claim 32, further comprising:
calculating melt velocity as a function of temperature and melt viscosity as a function of melt velocity.

34. The method of claim 28, wherein the thermal detector, pressure, sensor, processor and acoustic transmitter compose a sensor, the method further comprising embedding the sensor in an injection mold in an orientation enabling the sensor to sense temperature and pressure of a viscous material in the injection mold.

35. The method of claim 28, wherein converting the output from the infra-red thermal detector further includes converting the output from the infra-red thermal detector to the melt velocity based on a rate that a lens of the infra-red thermal detector is covered.

36. The method of claim 35, wherein the infra-red thermal detector data is arranged to measure flow of material being measured in a direction normal to the flow of material.

37. An apparatus for a manufacturing process, the apparatus including:
a sensor configured to detect parameters associated with a manufacturing process, the parameters including pressure, temperature, and at least one of melt velocity and melt viscosity;
a receiver configured to recognize the parameters; and
a control module configured to adjust the manufacturing process in response to the parameters received.

* * * * *